US006492122B2

(12) United States Patent
Weidenhammer et al.

(10) Patent No.: US 6,492,122 B2
(45) Date of Patent: Dec. 10, 2002

(54) QUANTITATIVE ANALYSIS METHODS ON ACTIVE ELECTRONIC MICROARRAYS

(75) Inventors: Elaine M. Weidenhammer, San Diego, CA (US); Ling Wang, San Diego, CA (US); Xiao Xu, San Diego, CA (US); Michael J. Heller, Encinitas, CA (US); Brenda F. Kahl, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/975,408

(22) Filed: Oct. 10, 2001

(65) Prior Publication Data

US 2002/0150917 A1 Oct. 17, 2002

Related U.S. Application Data

(62) Division of application No. 09/710,200, filed on Nov. 9, 2000, now Pat. No. 6,379,897.

(51) Int. Cl.[7] .......................... C12Q 1/68; C12P 19/34; C12M 1/34; C07H 21/02; C07H 21/04
(52) U.S. Cl. .......................... 435/6; 435/71; 435/91.1; 435/91.2; 435/287.2; 536/22.1; 536/23.1; 536/24.3; 536/24.31; 536/24.32; 536/24.33
(58) Field of Search ............... 435/6, 7.1, 91.1, 435/91.2, 287.2; 536/22.1, 23.7, 24.3–24.33

(56) References Cited

U.S. PATENT DOCUMENTS

| | | | |
|---|---|---|---|
| 4,683,195 A | 7/1987 | Mullis | 435/6 |
| 4,851,331 A | 7/1989 | Vary | 435/6 |
| 5,137,806 A | 8/1992 | LeMaistre | 435/6 |
| 5,219,727 A | 6/1993 | Wang | 435/6 |
| 5,262,311 A | 11/1993 | Pardee | 435/91.2 |
| 5,399,491 A | 3/1995 | Kacian | 435/91.21 |
| 5,503,980 A * | 4/1996 | Cantor | |
| 5,512,439 A | 4/1996 | Hornes | 435/6 |
| 5,545,522 A | 8/1996 | Van Gelder | 435/6 |
| 5,580,726 A | 12/1996 | Villeponteau | 435/6 |
| 5,599,672 A | 2/1997 | Liang | 435/6 |
| 5,605,662 A | 2/1997 | Heller | 422/68.1 |
| 5,632,957 A | 5/1997 | Heller | 422/68.1 |
| 5,643,765 A | 7/1997 | Willey | 435/91.2 |
| 5,658,736 A | 8/1997 | Wong | 435/6 |
| 5,665,547 A | 9/1997 | Pardee | 435/6 |
| 5,700,667 A | 12/1997 | Marble | 435/91.3 |
| 5,707,807 A | 1/1998 | Kato | 435/6 |
| 5,710,029 A | 1/1998 | Ryder | 435/91.1 |
| 5,716,785 A | 2/1998 | Van Gelder | 435/6 |
| 5,723,290 A | 3/1998 | Eberwine | 435/6 |
| 5,753,439 A | 5/1998 | Smith | 435/6 |
| 5,783,391 A | 7/1998 | Rossi | 435/6 |
| 5,849,486 A | 12/1998 | Heller | 435/6 |
| 5,866,330 A | 2/1999 | Kinzler | 435/6 |
| 5,869,249 A | 2/1999 | Rossi | 435/6 |
| 5,876,932 A | 3/1999 | Fischer | 435/6 |
| 5,908,744 A * | 6/1999 | McAllister et al. | |
| 5,965,452 A | 10/1999 | Kovacs | 436/149 |
| 5,968,784 A | 10/1999 | Spinella | 435/91.1 |
| 5,981,190 A | 11/1999 | Israel | 435/6 |
| 5,994,076 A | 11/1999 | Chenchik | 435/6 |
| 6,004,755 A | 12/1999 | Wang | 435/6 |
| 6,013,431 A | 1/2000 | Soderlund | 435/5 |
| 6,017,696 A | 1/2000 | Heller | 435/6 |
| 6,027,923 A | 2/2000 | Wallace | 435/91.2 |
| 6,040,138 A | 3/2000 | Lockhart | 435/6 |
| 6,048,690 A | 4/2000 | Heller | 435/6 |
| 6,051,380 A | 4/2000 | Sosnowski | 435/6 |
| 6,068,818 A | 5/2000 | Ackley | 422/50 |
| 6,071,394 A | 6/2000 | Cheng | 204/547 |
| 6,099,803 A | 8/2000 | Ackley | 422/68.1 |
| 6,129,828 A | 10/2000 | Sheldon, III | 204/518 |

FOREIGN PATENT DOCUMENTS

| | | |
|---|---|---|
| EP | 1 043 405 A2 | 10/2000 |
| WO | WO9712030 | 4/1997 |
| WO | WO9801758 | 1/1998 |
| WO | WO9810273 | 3/1998 |
| WO | WO9810277 | 3/1998 |
| WO | WO9851819 | 11/1998 |
| WO | WO9929711 | 6/1999 |
| WO | WO9938612 | 8/1999 |
| WO | WO9942558 | 8/1999 |
| WO | WO9943853 | 9/1999 |
| WO | WO0032744 | 6/2000 |
| WO | WO0037163 | 6/2000 |
| WO | WO0058522 | 10/2000 |
| WO | WO0060919 | 10/2000 |
| WO | WO0061720 | 10/2000 |
| WO | WO0061803 | 10/2000 |
| WO | WO0061805 | 10/2000 |
| WO | WO0061816 | 10/2000 |
| WO | WO0061817 | 10/2000 |
| WO | WO0061818 | 10/2000 |
| WO | WO0062036 | 10/2000 |
| WO | WO0106496 A1 | 1/2001 |

OTHER PUBLICATIONS

DeRisi et al., "Use of a cDNA Microarray to Analyse Gene Expression Patterns in Human Cancer", *Nature Genetics* 14: 457–460 (1996).

Higuchi et al., "Simultaneous Amplification and Detection of Specific DNA Sequences", *Bio/Technology*, 10: 413–417 (1992).

(List continued on next page.)

*Primary Examiner*—Jeffrey Siew
(74) *Attorney, Agent, or Firm*—O'Melveny & Myers LLP

(57) ABSTRACT

The present invention presents techniques useful in methods for gene expression monitoring, and other nucleic acid hybridization assays, that utilize microelectronic arrays to drive the transport and hybridization of nucleic acids. Particularly, methods for normalizing the signals of individual microlocations by the use of an internal control sequence probe are provided. These methods are particularly useful for hybridization assays in which a quantitative comparison of the hybridization of several different sequences at a plurality of microlocations is desired, such as in gene expression analyses.

14 Claims, 8 Drawing Sheets

OTHER PUBLICATIONS

Holland et al., "Detection of Specific Polymerase Chain Reaction Product by Utilizing the 5' → 3' Exonuclease Activity of *Thermus Aquaticus* DNA Polymerase", *Proc. Natl. Acad. Sci. USA*, 88: 7276–7280 (1991).

Hubank et al., "Identifying Differences in mRNA Expression by Representational Difference Analysis of cDNA", *Nucleic Acids Research*, 22: 5640–5648 (1994).

Lee et al., "Allelic Discrimination by Nick–Translation PCR With Fluorogenic Probes", *Nucleic Acids Research*, 21: 3761–3766 (1993).

Liang et al., "Differential Display of Eukaryotic Messenger RNA by Means of the Polymerase Chain Reaction", *Science*, 257: 967–971 (1992).

Schena et al., "Quantitative Monitoring of Gene Expression Patterns with a Complementary DNA Microarray," *Science*, 270: 467–470 (1995).

Scott et al., "Activation of Mouse Genese in Transformed Cells", *Cell*, 34: 557–567 (1983).

Velculescu et al., "Serial Analysis of Gene Expression", *Science*, 270: 484–487 (1995).

Zhao et al., "High–Density cDNA Filter Analysis: A Novel Approach For Large–Scale, Quantitative Analysis of Gene Expression", *Gene*, 156: 207–213 (1995).

* cited by examiner

FIGURE 6

|  | cIL1 | cTGFβ | cNS |
|---|---|---|---|
| Uninduced cells: IL1,TGFβ | | | |
| Induced cells: IL1,TGFβ | ● | ● | ● |
| Uninduced cells: IL6,JUN | ● | | ● |
| Induced cells: IL6,JUN | ● | ● | ● | cIL6  cJUN  cNS

QUANTITATIVE ANALYSIS METHODS ON ACTIVE ELECTRONIC MICROARRAYS

This application is a divisional of U.S. patent application Ser. No. 09/710,200, filed on Nov. 9, 2000, now U.S. Pat. No. 6,379,897 Apr. 30, 2002.

FIELD OF THE INVENTION

The present invention presents methods for gene expression monitoring that utilize microelectronic arrays to drive the transport and hybridization of nucleic acids. Procedures are described for generating mRNA expression samples for use in these methods from populations of cells, tissues, or other biological source materials, that may differ in their physiological and/or pathological state. Provided in the invention are methods for generating a reusable nucleic acid transcript library from mRNA in a sample of biological material. In order to improve gene expression monitoring on the microelectronic arrays, the transcripts are amplified to produce sample nucleic acid amplicons of a defined length. Because multiple sample amplicons may be selectively hybridized to controlled sites in the electronic array, the gene expression profiles of the polynucleotide populations from different sources can be directly compared in an array format using electronic hybridization methodologies. Also provided in the invention are methods for detecting the level of sample amplicons using electronically assisted primer extension detection, and utilizing individual test site hybridization controls. The hybridization data collected utilizing the improved methods of the present invention will allow the correlation of changes in mRNA level with the corresponding expression of the encoded protein in the biological source material, and thus aid in studying the role of gene expression in disease.

BACKGROUND OF THE INVENTION

The human genome contains approximately 100,000 genes. These genes are expressed at vastly different levels; the majority of species, over 90%, are present at low abundance, i.e. at five to fifteen copies per cell, while a few high abundance genes are expressed at thousands of copies per cell. In addition to the different levels of basal expression, gene expression is modulated in response to cell state, cell type, extracellular environment, disease, etc. Thus, information on changes in the levels of genes will enable a greater understanding of the pathological and/or physiological state of the organism under conditions of interest.

A number of methods currently exist for analyzing the expression levels of different messenger RNA (mRNA) species. Subtractive hybridization was used early in the history of monitoring of gene expression to analyze differences in levels of gene expression in different cell populations (Scott, et al.). This technique is not sufficiently sensitive to detect messages present at low levels in a polynucleotide population. Representational difference analysis is a more recent modification that includes amplification after subtraction, in order to detect mRNAs that are expressed at low levels (Hubank and Schatz). While this method allows identification of differentially expressed messages that are present at low levels, the amplification step makes quantification difficult.

Adaptations of the polymerase chain reaction (PCR) have proven valuable in the field of gene expression. Reverse transcription coupled with competitive PCR (Competitive RT-PCR) involves co-amplifying a known amount of an exogenous RNA competitor with the target mRNA sequence (Gilliland, et al.). The amount of target is extrapolated from a titration curve based on the concentration of competitor. The difficulties with this technique lie in the limited dynamic range of the assay and the tedium of constructing separate competitors for each target of interest.

Real-time PCR is a powerful approach for gene expression monitoring. The original method detected accumulation of double stranded species during amplification using ethidium bromide and an adapted thermocycler (Higuchi, et al.); detection of non-specific products was a drawback that was subsequently overcome by designing of probes that generate signal only if the target of interest is amplified (Holland, et al.; Lee, et al.). This approach requires that the linear ranges of amplification are similar for abundant internal controls and endogenous target mRNAs that may be present at much lower levels. In addition, primer design is critical and requires special software programs for optimal efficiency.

Differential display PCR (dd-PCR) is also a PCR-based method that has been adapted for monitoring gene expression. The original protocol used sets of random, anchored primers to amplify all mRNAs in two different cell populations; differences in levels are visualized by separating the PCR product on denaturing polyacrylamide gels (Liang and Pardee). Many variations on this original technique have been devised. In general, however, the PCR-based amplification of these methods results in a lack of quantitative correlation of band intensity with message abundance, variable reproducibility, and a high level of false positives. Results generated by dd-PCR must therefore be confirmed by other methods.

Serial analysis of gene expression (SAGE) is another technique for gene expression monitoring. Short sequence tags that uniquely identify the mRNA transcripts in a given cell population are isolated, concatenated, cloned and sequenced (Velculescu, et al.). The frequency of any given tag reflects the abundance of the corresponding transcript. This technique, while powerful, is rather complicated, requires generation and analysis of large amounts of sequence data, and the amplification event can skew quantitation.

The most recent developments in the field are in the area of microarrays (Schena, et al.; DeRisi, et al.; Zhao, et al.). Gene-specific probes are individually arrayed on a solid matrix and incubated with labeled cDNAs from control and experimental populations. Comparison of the intensity of probe hybridization with cDNA targets from the distinct samples reveals differences in expression of the corresponding mRNAs. Because these arrays are hybridized passively in a low stringency buffer, differences in availability of relevant target sequences to the complimentary probes on the array may not be uniform. In addition, hybridization characteristics of each probe will vary, due to $T_m$ considerations and the affinity of probe-target interactions. Therefore, while these high-density microarrays offer high-throughput, the hybridization kinetics may not be optimal for all different probe-target combinations.

Although great strides have been made in methods to detect alterations in gene expression, each of the procedures has drawbacks as well as advantages, as indicated above. All of the above approaches are either time consuming, complicated, labor intensive, or a combination of all three. Rapid, sensitive approaches that allow simultaneous monitoring of multiple mRNAs are still needed.

SUMMARY OF THE INVENTION

The present invention provides a method that allows efficient electronic hybridization of amplified nucleic acids generated from target mRNAs to complementary probes in a microarray format. The use of electric fields to transport and drive hybridization of nucleic acids allows the rapid analysis of polynucleotide populations. Utilizing electronic hybridization devices, such as those described in U.S. Pat. No. 5,605,662, hybridization assays may be accomplished in as little as 1–5 minutes. Additionally, because each site on the microarray is individually controlled, targets from different samples can be analyzed on the same matrix under optimized conditions, an aspect unique to this technology. By improving the use of electronic hybridization methods and devices in gene expression monitoring applications, the disclosed methods will dramatically increase the ability of those in the art to rapidly generate gene expression information with a minimum of sequence-specific optimization.

The methods of the invention facilitate the use of electronically hybridized gene expression monitoring for both research and clinical applications in several ways. First, through the use of shortened amplicons of uniform size, the methods of the invention allow the rapid, simultaneous monitoring of dozens of genes in comparative and quantitative procedures with minimal interference from cross-hybridization and secondary structure formation. Because the individual test sites in the electronic array may be selectively controlled, several samples may be screened on the same microarray in the same experiment. Preferred embodiments of the method for determining the level of mRNA expression in the cells of a biological sample include the steps of (a) isolating mRNA from at least one biological sample, (b) quantitatively amplifying from the isolated mRNA population at least two gene sequences of interest to produce shortened amplicons of less than about 300 bases in length, (c) electronically hybridizing the amplicons to at least two probes bound to a support at predetermined locations, and (d) determining the amount of each amplicon hybridized to each probe at the predetermined locations.

Although several equally desirable embodiments of the general method of the invention are provided, it is preferred that the quantitative amplification step of the method comprise a linear amplification step in which the sequences of interest are amplified from a fixed amount of template generated from the reverse transcription of the mRNA population isolated from the biological sample. Exemplary preferred processes include single primer DNA polymerase amplification and in vitro transcription amplification. The amplicons are preferably shortened during the amplification process through the use of matched sets of "bookending" primers which generate amplicons of a defined length, or by the utilization of an endogenous or introduced type IIs endonuclease site to cleave the amplicons at some point in the amplification process. The shortened amplicons produced for use in the methods of the present invention are preferably about 50 to about 300 bases in length, more preferably about 50 to about 200 bases in length, and most preferably about 50 to about 100 bases in length.

As the electronic hybridization processes of the method may be carried out on arrays of individually electronically controlled test sites, multiple genes may be monitored in multiple samples during a single experiment on the same electronic array device. At least two, at least ten, and even fifty or more samples may be assayed in a single experiment. Similarly, at least, 5, 10, 20, 40, or 50 or more different genes may be simultaneously monitored in an experiment. As electronic microarray devices with tens of thousands of test sites have been produced, and the electronic hybridization process can be completed in as little as 1–5 minutes, an experiment in which 80 genes are monitored in 100 different samples sequentially hybridized to rows of test sites on the array may be completed in a few hours.

Detection methods which may be used in the gene expression monitoring methods of the present invention include all commonly employed nucleic acid hybridization interaction detection methods such as primer extension labeling, amplicon labeling, reporter probe detection, and even intercalating dyes. The detectable moiety in these labeling methods may be a fluorophore, chemiluminescent, colorigenic, or other detectable moiety. Fluorophore moiety labels are preferred for use in the present invention because of their widespread availability and relative ease of use.

In as second aspect, the present invention provides methods for the use of reusable bead libraries produced from mRNA samples to extend the effective amount and life of precious biological and patient samples by allowing re-amplification of the same sample nucleic acids. Preferred embodiments of this method of the invention include the steps of: (a) isolating mRNA from a patient sample; (b) reverse transcribing a cDNA library from the mRNA isolate; (c) amplifying the cDNA library with a primer containing an upstream RNA polymerase promoter site upstream of a sequence specific for the mRNA of interest and a fill-in primer, wherein at least one of the primers comprises an affinity moiety; (d) binding the amplification products from (c) to a solid support coated with an affinity-binding moiety; (e) utilizing the bound amplification products as a template for an in vitro transcription reaction; (f) separating the in vitro transcription products from step (e) from the amplification products bound to the solid support; and (g) utilizing the bound amplification products from step (f) as a template for at least one additional in vitro transcription reaction, wherein the amount of in vitro transcription product produced is not significantly less than that produced in step (e).

In more preferred embodiments, steps (f) and (g) are repeated one, two, or even three or more times. As observed by applicants, the amount of transcript produced in successive rounds of in vitro transcription does not decrease significantly as compared to the amount of transcript produced in the proceeding round. Preferably, at least about 70%, more preferably at least about 80%, and most preferably at least about 90% of the amount of transcript produced in a preceding round of transcription is produced in a succeeding round.

Preferred affinity moieties for use in the reusable library method of the invention include biotin, haptens, and antigenic moieties. Biotin is particularly preferred, and in embodiments where biotin is the affinity moiety, streptavidin and avidin are preferred affinity-binding moieties. Preferred solid supports for use in the reusable library method include beads, microtiter wells, pins, and the like. Exemplary preferred beads include paramagnetic beads, polymer beads, and metallic beads.

In a third aspect, the present invention provides rapid detection methods for detecting the hybridization of target sequences to the electronic microarray without the need for additional reporter probes, or labeling of the target sequences, using primer extension reactions. Preferred embodiments of this method of the invention comprise the steps of (a) electronically hybridizing a nucleic acid in a sample to a nucleic acid probe bound to a support at a predetermined location; (b) utilizing the hybridized nucleic acid as a template in a nucleic acid polymerase reaction to extend the bound probe, thus incorporating a labeled nucleotide into the extended probe; and (c) detecting the labeled nucleotide incorporated into the extended bound probe.

Preferred labeling moieties for the labeled nucleotide include fluorescent moieties, colorigenic moieties, chemiluminescent moieties, and affinity moieties. Fluorescent moieties are particularly preferred. Nucleic acid polymerase reactions which may be used in the method include DNA polymerase reactions (where the hybridized nucleic acid is DNA) and reverse-transcriptase reactions (where the hybridized nucleic acid is RNA).

A fourth aspect of the present invention is a method of providing an internal control for individual test sites on an electronically controlled microarray for use in nucleic acid hybridization reaction assays for determining the presence of nucleic acid sequences in nucleic-acid-containing samples. Such internal controls are useful for real-world applications of microarray technology because of the inherent irregularities introduced by the microfluidics systems which distribute the sample and reagents to the surface of the microarray. Preferred embodiments of the method comprise the steps: (a) attaching a mixed nucleic acid probe consisting of a first nucleic acid probe specific for a first nucleic acid sequence known to be present in the sample (e.g., endogenous or spiked), and a second nucleic acid probe specific for a second nucleic acid sequence of interest to a first test site on the electronically controlled microarray; (b) attaching a mixed nucleic acid probe consisting of the first nucleic acid probe and a third nucleic acid probe specific for a third nucleic acid sequence of interest, which may be the same as or different than the second nucleic acid sequence, to a second test site; (c) electronically hybridizing the sample nucleic acids to the nucleic acid probes on the first and second test sites; (d) specifically detecting the extent of hybridization of the sample nucleic acids to the first nucleic acid probe at the first and second test sites; (e) specifically detecting the extent of hybridization of the sample nucleic acids to the second and third nucleic acid probes at the first and second test sites; (f) comparing the hybridization values obtained for the first nucleic acid probe at the first and second test sites to obtain a normalization factor; and (g) normalizing the hybridization values obtained in (e) for the second and third probes using the normalization factor obtained in (f).

Preferred embodiments of the internal control methods of the invention utilize an endogenous "housekeeping" gene sequence, which is known to be maintained at a steady-state level across the relevant sample cell types, as the first control sequence. Alternatively, exogenous nucleic acid sequence may be added to the sample at known concentrations. The detection methods utilized to specifically detect the hybridization of the sample nucleic acids to the first and the second and third nucleic acid probes may be independently chosen from any standard detection method, including the labeling of amplified sample nucleic acids through sequence specific primers, primer extension detection, hybridization of reporter probes to bound sample nucleic acids, or a combination of these methods. In order for hybridization to the first nucleic acid probe to be distinguishably detectable from hybridization to the second and third nucleic acid probes, it is desirable to use two easily distinguishable detectable moieties. Preferred detectable moieties for use in the internal control method are fluorescent moieties with different emission wavelengths. Alternatively, the extent of hybridization to the first (control) probe may be determined first using a detectable moiety after performing a first selective labeling method, and then the extent of hybridization to the second and third probes determined after a second selective labeling method with the same detectable moiety by determining the increase in the detectable signal.

BRIEF DESCRIPTION OF THE FIGURES

FIG. 6: Shown are grayscale hybridization fluorescence data for four separate gene probes and a control sequence (NS) on twelve test sites on a NanoChip™. mRNA was isolated from LPS induced and uninduced monocytes; amplification, hybridization and reporting were carried out as described in Example 5. The treated monocytes clearly show an altered mRNA expression level in IL1, TGFβ, and JUN, while the expression level of IL6 is only slightly increased.

DEFINITIONS

Figure 1:
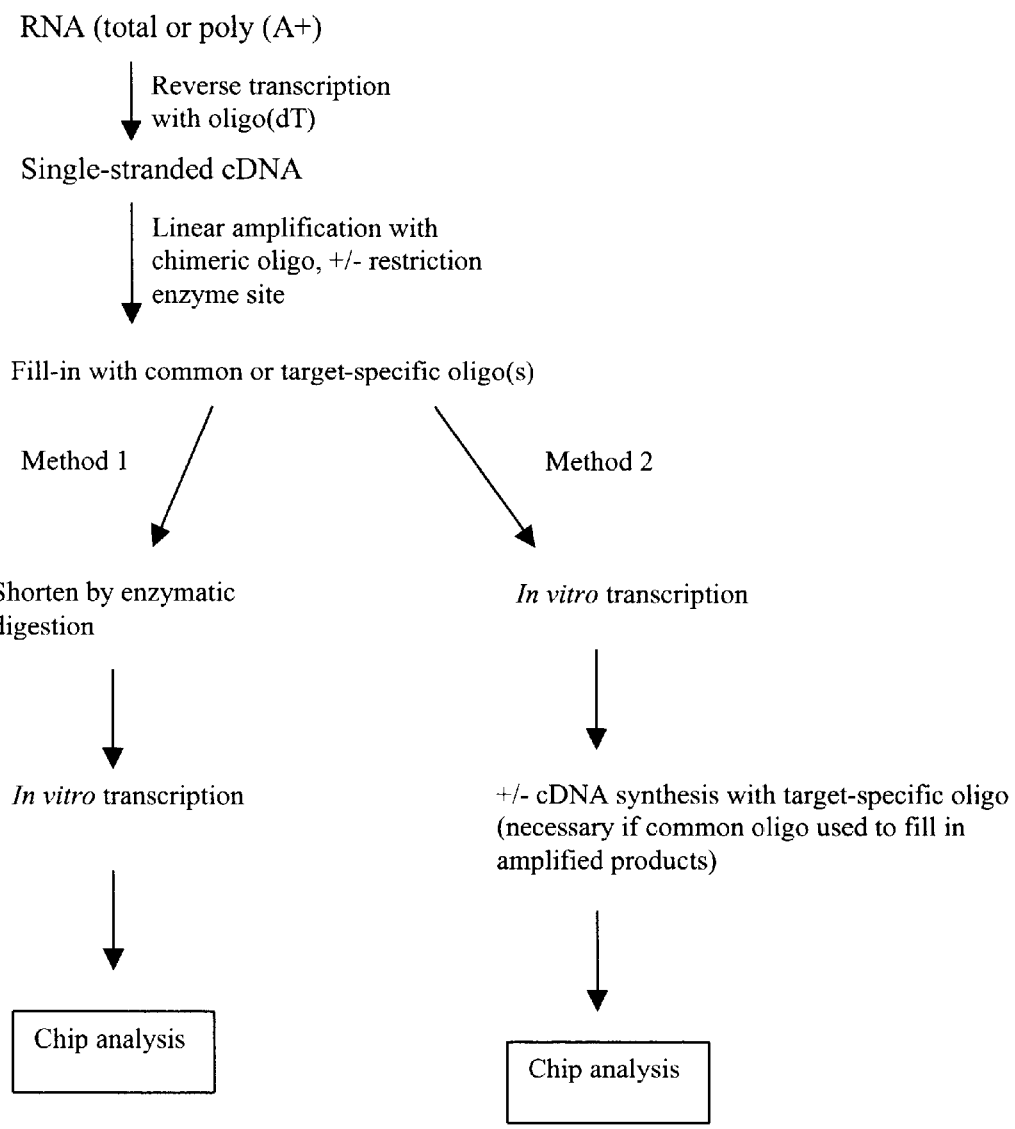
FIG. 1: A schematic of two alternative methods for generating shortened amplicons of a defined size for use in the mRNA gene expression monitoring methods of the invention.

As used herein, "nucleic acid" refers to any nucleic acid polymer, including deoxyribonucleic and ribonucleic acid polymers, including modified DNA or RNA, including synthetic oligonucleotides, peptide nucleic acids (PNA), pyranosyl nucleic acids (pRNA), and derivatives of these nucleic acids.

"Amplicon," as used herein, denotes an amplified nucleic acid sequence which may be either RNA or DNA, depending on the amplification method used (e.g., DNA PCR produces a DNA amplicon, while in vitro transcription produces an RNA amplicon.) The amplified nucleic acid sequence comprises either the same or complementary sequence as that of the original nucleic acid sequence which was amplified. "Shortened amplicon" denotes an amplicon which contains a portion of the full endogenous nucleic acid sequence rather than the whole sequence.

"Electronic hybridization" means the use of electric fields to concentrate nucleic acids within a certain area in order to reduce the time necessary to hybridize complementary nucleic acids. Electronic hybridization is advantageously performed using electronically controlled microarray devices, such as those described in U.S. Pat. No. 5,605,662. These devices comprise individually controllable electrodes which are covered by a permeation layer, or layer of material which permits ion exchange between the buffer and the electrode, but which inhibits contact between nucleic acids in the buffer and the electrode. Nucleic acid capture probes may be advantageously attached to binding moieties within or on the permeation layer of these electronic array devices.

"Gene," as used herein, means an organismal nucleic acid sequence encoding a protein, such as genomic DNA or mRNA (including splicing variants), or a copy or portion thereof produced by molecular genetic manipulations, such as cDNA, in vitro transcribed RNA, cloned DNA, etc. As used herein "target" generally refers to a gene of interest.

"Amplification," as used broadly herein, encompasses various processes and sets of processes (including: reverse transcription, DNA polymerase reactions, ligase reactions, in vitro transcription, and combinations thereof) for copying nucleic acids (either in their original deoxyribonucleotides or ribonucleotides, or other natural or artificial nucleotides) through molecular genetic manipulations. "Linear amplification" or "quantitative amplification" refers to processes and sets of processes for producing copies of nucleic acids from a substantially constant amount of template, so that the number of copies of the nucleic acid, or its complement, increases linearly as a function of time, rather than exponentially.

DETAILED DESCRIPTION OF INVENTION

The methods described are designed to determine the abundance of target genes in a distinct polynucleotide population, particularly as compared to the abundance of those target genes within a different polynucleotide population. The methods of this invention are particularly suited for gathering data to correlate differences in expression patterns with specific physiological and/or pathological states. Electronic nucleic acid hybridization techniques and devices (such as those described in U.S. Pat. No. 5,605,662, incorporated herein in its entirety), are capable of dramatically reducing the time necessary to perform various nucleic acid hybridization procedures, and are thus an extremely useful tool for a wide variety of biological assay methods. The methods of this invention enable those of skill in the biochemical arts to more fully exploit this tool to study the expression of genes in organisms under various physiological conditions.

In the methods of this invention, target genes are quantitatively amplified from mRNA populations derived from any biomaterial, including, but not limited to, cells from unicellular organisms, cells derived from in vitro cultured cell lines, and cells or tissues from multicellular organisms. In one preferred embodiment, the amplified target genes (amplicons) are enzymatically shortened using a type IIs restriction endonuclease. In another preferred embodiment, generation of shortened amplicons is mediated via sequence specific oligonucleotides which "bookend" the amplified sequence. Shortened amplicons are analyzed by electronic hybridization to capture probes comprising complementary nucleic acids that are specific for each target gene of interest. These capture probes are preferably immobilized in a microarray format. Detection of the hybridized targets may be performed by primer extension of the capture probe, or by hybridization of a second complementary species that is labeled, or by other means.

An important aspect of the invention is the generation of target nucleic acid sequences which are of similar size and/or reduced length. The efficiency and uniformity of electronic hybridization is increased when targets are limited in size. In addition, efficient analysis of different targets is facilitated if the target species are similar in size because variations in electronic transport and hybridization of different targets are reduced. Further, when the target(s) being examined comprise single stranded nucleic acids, particularly ribonucleic acids, secondary structure considerations are minimized by reduced length. Gene expression monitoring on electronic microarrays is thus improved by utilization of shortened targets of relatively uniform size, as is demonstrated in the data of Table 1.

mRNA Isolation and cDNA Library Preparation

The initial step in the subject invention is isolation of a sample of polynucleotides, usually mRNA, from populations of interest. The polynucleotide populations may be derived from a variety of sources, including but not limited to different cell types from in vitro cultured cell lines or different cell types from organs or tissues of multicellular organisms, or the same cell type from different organisms of the same species. The polynucleotide populations may also be derived from the same cell type from in vitro cultured cell lines or from an organ or tissue of a multicellular organism, at different stages of development, disease, or treatment.

After isolation by standard means well known to those of skill in the molecular genetics arts, reverse transcription is performed to generate single-stranded cDNA from the mRNA population. cDNA synthesis can be performed by any method known to those of skill in the art. The various dNTPs, buffer medium, and enzyme with reverse transcriptase activity may be purchased commercially from various sources. Applicants have found the Superscript™ enzyme system to be well suited for the production of an initial cDNA library. First strand synthesis may be directed by an oligo(dT) primer that hybridizes to all polyadenylated RNA species. The oligo(dT) primer is usually 10–30 bases long, more preferably 12–18 bases long, and may comprise a mixture of primers of different lengths. Other suitable polythymine primers include the non-replicable dT primer described in U.S. Pat. No. 6,027,923, and oligo(dT)$_n$V (V=A, C, or G) primers.

Quantitative Shortened Amplicon Generation: Primer Extension and in vitro Translation Techniques In transcription-amplification embodiments of the invention, the generation of amplicons is accomplished through the use of a chimeric oligonucleotide specific to each target of interest. Following cDNA synthesis, the target(s) of interest may be linearly amplified by primer extension of a chimeric oligonucleotide(s) using DNA polymerase. Linear amplification either by primer extension, as here, or by other means (such as in vitro transcription, used below), is necessary in order to allow quantitative comparisons between different samples. The sequence specific portion of the chimeric oligonucleotides are sufficiently specific as to anneal to the complementary target sequence under conditions of primer extension by a polymerase reaction (DNA polymerase if produced from a cDNA library), which are familiar to those of skill in the molecular biology arts. In order to generate target amplicons for the gene sequences of interest, one chimeric oligonucleotide specific to each target of interest is used. These oligonucleotides contain an RNA polymerase promoter sequence at the 5' end; this sequence may be the consensus binding site for T7, T3, SP6, or another RNA polymerase. Adjacent to the RNA polymerase promoter site is a sequence specific to the target gene of interest. This gene-specific sequence is not restricted in length; however, to promote efficient annealing of the chimeric oligonucleotide(s) to the target(s) of interest, the gene-specific sequence will preferably be between 15 and 35 bases in length. The oligonucleotides may contain a biotin moiety at the 5' end, or may be unmodified. In embodiments utilizing a type IIs endonuclease for shortened amplicon generation, the chimeric primer will also contain, at the 3' end, the recognition sequence for a type IIs restriction endonuclease.

The sets of chimeric oligonucleotides that are used in target preparation will generally represent at least two distinct target species but may represent 10, 20, 40, or even up to 50 distinct target species. Above about 50 different target species, amplification efficiency and the quantitative nature of the results may be compromised, utilizing currently available amplification techniques. However, the use of the present invention with improved amplification techniques to measure, potentially, 80, 90 or over 100 specific genes simultaneously is also contemplated by the present methods. The chimeric oligonucleotides are typically chosen to represent targets that are known or suspected to be differentially expressed under the experimental conditions (e.g., cell type, or two different stimuli for a single cell type), or may represent targets for which no expression data are available. One of the chimeric oligonucleotides in the set is chosen to allow analysis of levels of a housekeeping gene that is known to be expressed at similar levels in the different conditions being examined, or of an added exogenous control sequence.

Examples of commonly used housekeeping genes include glyceraldehyde phosphate dehydrogenase (GAPDH), β-actin, and ribosomal RNAs. Controls can also comprise exogenous sequences that are added into the starting material at known concentration and processed along with the targets of interest. An example of such sequence is the β-lactamase gene, a prokaryotic gene that confers ampicillin resistance. (For review, see Reischl, U. and Kochanowski, B. (1999) "Quantitative PCR" *Quantitative PCR Protocols* (pp.3–30). Humana Press., Totowa, N.J.; and also Ferre F. (1992) Quantitative or semi-quantitative PCR: Reality versus myth. PCR Methods Appl. 2, 1–9.) The selection of a particular control sequence for use in an application of the described methods will be case specific, depending on the organism used, the particular cells studied, and the familiarity of the researcher with a particular constitutively expressed sequence. However, using the guidelines presented, one of ordinary skill in the art could readily select an endogenous or exogenous sequence for use as a control in the present methods.

Single-primer extension may be directed by a thermophilic DNA polymerase, usually a 3'–5' exonuclease-minus derivative polymerase, e.g. Vent®$_R$(exo-) DNA polymerase. Multiple copies of the target(s) are generated during the extension reaction, in which repeated cycles of denaturation, oligonucleotide primer annealing, and DNA polymerase-directed primer extension are performed. Following generation of multiple single-stranded copies of target(s) from the cDNA pool, the complementary strands are generated. In one embodiment, generation of the complementary strand is mediated by a common primer that binds to all amplified targets. This primer may be the oligo(dT) oligonucleotide used for first strand cDNA synthesis, a fraction of which is carried over from the first strand cDNA synthesis reaction into the primer extension reaction. Alternatively, the primer may be a mixture of random short polynucleotide sequences, e.g. random hexamer primers. In this embodiment, the primer is allowed to anneal at a temperature corresponding to the Tm of the primer used for second strand synthesis. In another embodiment, a gene-specific oligonucleotide for each target of interest is utilized, yielding a "bookended" product, as described further below. This primer will generally be 15–30 bases in length and will hybridize at a specific site within the amplified target such that the second strand produces an amplicon of a defined length. The primers may contain a biotin moiety at the 5' end, or may be unmodified. Primers are allowed to anneal at or slightly below the lowest Tm among the primers in the set. After allowing sufficient time for the primers to anneal, the temperature is increased to allow efficient extension of the primers by the thermophilic DNA polymerase.

Shortening of Amplicons by Type IIs Endonuclease Cleavage or Bookending

Amplicons for use in the present invention preferably are less than about 300 bases, more preferably less than about 200 bases, and most preferably less than about 100 bases. Because the amplicon must be of a sufficient size to hybridize specifically to the capture probe, amplicons are preferably greater than 15 bases in length, and are more preferably at least about 50 bases in length. In addition, although the amplicons for use in the methods of the invention may differ significantly in length, it is preferred that they be of similar length, preferably differing in length by less than 20 bases, and more preferably differing in length by less than 10 bases. The generation of shortened amplicons may be accomplished through the use of Type IIs endonucleases, or by the use of primers designed to "bookend" a stretch of the target sequence. Although both methods are described below, other methods may be devised by those of skill in the art. The use of shortened amplicons made by alternative amplification strategies in the methods of the present invention is contemplated to be within the scope of those methods, so long as a shortened, quantitatively amplified nucleic acid is produced from the sample mRNA.

In a first strategy, shortening of the target nucleic acid sequences is performed by digestion with a type IIs restriction endonuclease. Type IIs restriction endonucleases cleave at a defined distance from the recognition site, thus producing a gene-specific "tag" that can subsequently be used to isolate and quantify each target. For this embodiment, a type IIs restriction endonuclease recognition site is incorporated at or near the 3' end of the chimeric oligonucleotide used for amplification, supra. Where possible, this sequence will be present in the target(s) of interest, and the chimeric oligonucleotide(s) will be designed to utilize the endogenous restriction endonuclease recognition sequence. In this case, the gene-specific portion of the oligonucleotide(s) will anneal to the restriction endonuclease recognition site and sufficient adjacent sequence 5' of the recognition site to produce an amplicon of the desired length upon cleaving.

Where an endogenous type IIs restriction enzyme recognition site is not present in the target of interest, a sequence within the target will be chosen that resembles the desired site as closely as possible, with preference given to sequences that perfectly match the 3' end of the endonuclease recognition site. The chimeric oligonucleotide will then be designed to generate the desired restriction endonuclease recognition site by altering the target sequence during primer extension. Such alterations may include changing, inserting or deleting nucleotides as necessary to generate a type IIs restriction endonuclease recognition site into the amplified target.

The proximity of the restriction endonuclease recognition site to the 3' end of the chimeric oligonucleotide will in part be determined by whether a site exists within the targets of interest or whether such site must be generated within the chimeric oligonucleotide. If an endogenous site is used, the chimeric oligonucleotide may end at the last base pair of the restriction endonuclease recognition site or may include additional target-specific sequence. In the case where the target sequence must be altered to generate a restriction endonuclease recognition site, the chimeric oligonucleotide will generally, although not necessarily, extend beyond the restriction endonuclease recognition site in order to permit the mutated oligonucleotide sequence to efficiently anneal to the target. The extension, if any, will preferably be only a few bases in length, in order to ensure that sufficient target sequence is retained upon cleavage by the Type IIs endonuclease.

Digestion with the type IIs restriction endonuclease will yield target fragments that contain the RNA polymerase promoter sequence followed by the target-specific sequence contained within the chimeric primer, plus the target-specific sequence that lies between the type IIs restriction enzyme recognition site and the type IIs restriction enzyme cleavage site. If the chimeric oligonucleotide contains a biotin moiety at the 5' end, the digested fragments may at this point be isolated using streptavidin-coupled magnetic beads; alternatively, the Vent-amplified material can be applied to the streptavidin-coupled magnetic beads for purification prior to restriction enzyme digestion. If a biotinylated 3' gene-specific oligonucleotide is used to fill in the amplified single-stranded products, targets can be applied to streptavidin-coupled magnetic beads prior to digestion and thereby isolated from any nonspecific materials. Subsequent to enzymatic digestion, the 5' ends of the targets can be isolated away from the bead-bound 3' ends of the amplified targets.

Subsequent to digestion, target fragments are used as templates in in vitro transcription reactions mediated by a RNA polymerase, the promoter sequence for which was incorporated via the chimeric oligonucleotide. Standard methods for in vitro transcription are known to those of skill in the art. In the case where biotinylated chimeric oligonucleotides were used to generate amplified target, multiple rounds of in vitro transcription can be performed; the bead-bound templates can also be stored for future in vitro transcription reactions. In vitro transcribed templates are then cleaned and desalted by any standard method including, but not limited to, gel filtration columns.

In an alternative strategy, shortened targets are generated via oligonucleotide primers rather than by endonuclease digestion. In the case where oligo(dT), random primers, or gene specific oligonucleotides were utilized to fill in the single-stranded amplified target(s), in vitro transcription reactions are performed after the fill-in reaction. When a gene-specific oligonucleotide is used to generate the second strand, this primer is designed to hybridize to a sequence within the target at a defined length from the 5' end, generally less than about 300 base pairs away. In this "early bookending" embodiment, the RNA produced in the in vitro transcription reaction is sufficiently shortened such that the amplified material can be directly analyzed by electronic hybridization. Alternatively, the shortened RNA products may be subjected to another round of cDNA production and DNA polymerase mediated amplification utilizing gene-specific or random primers.

Figure 2:
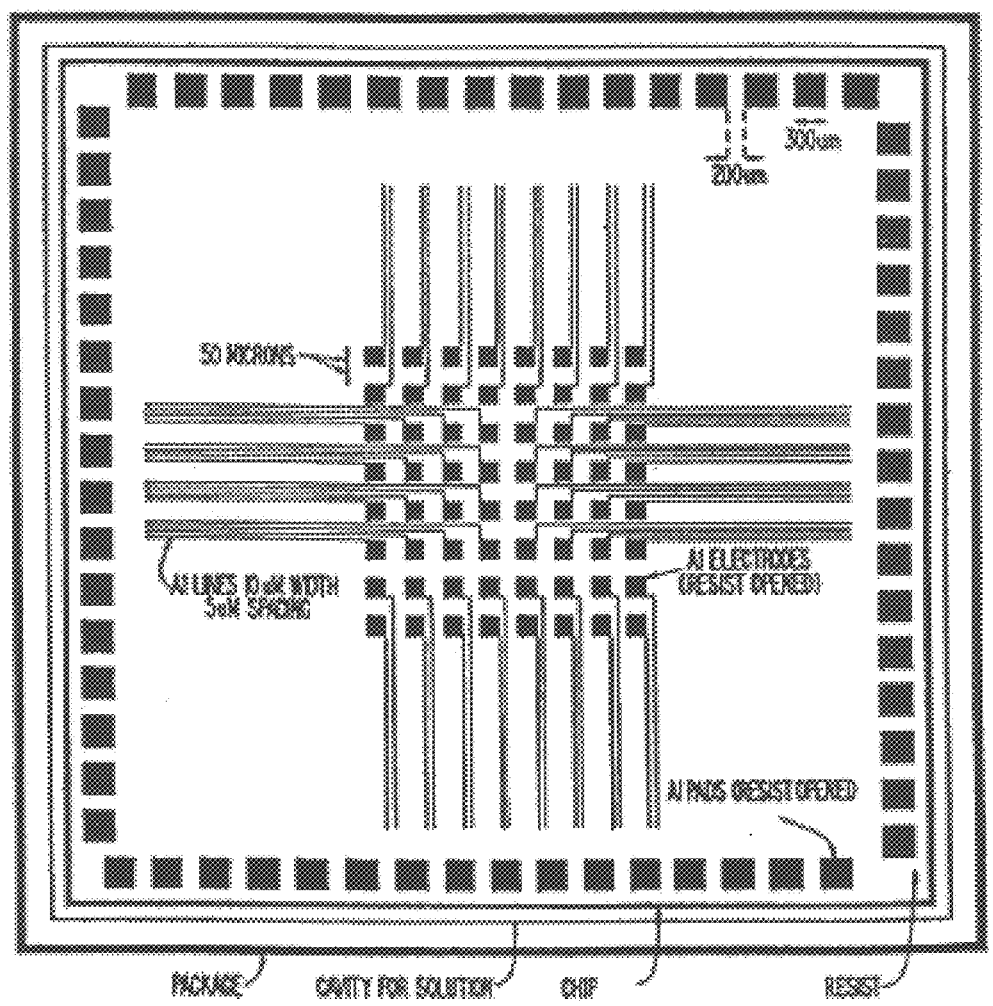
FIG. 2: A schematic of an electronically addressable microarray device which is similar to the device used in the Examples. The depicted device is described in detail in U.S. Pat. No. 5,605,662. Note that in this device the test sites on the array are defined in the plane of the array by the electrodes, but are separated from the electrodes by a permeation layer, to which nucleic acid probes may be attached.

In the case where oligo(dT) or a set of primers of random sequence is utilized to fill in the amplified target(s), in vitro transcription will yield RNAs of variable length, some of which may be too short to be recognized by the capture oligonucleotide used in electronic hybridization, as described infra, and some of which may be too long to be efficiently electronically transported and hybridized. In order to improve detection of these target(s), the RNA derived from the in vitro transcription reaction is used as a template for a second cDNA synthesis reaction. For this method, a gene-specific oligonucleotide specific for each target of interest is used to prime cDNA synthesis. This primer will generally be 15–30 bases in length and will hybridize at a specific site within the amplified target such that the second strand is of a defined length, generally less than about 300 base pairs, more preferably about 50 to about 300 bases, more preferably from about 50 to about 200 bases, and most preferably from about 50 to about 100 bases. This reverse transcription reaction is performed using reagents and methods known to those of skill in the art, as described supra. The products of this reaction will comprise shortened amplicons for each target of interest Electronic Hybridization of Shortened Amplicons Analysis of target(s) is performed on microarrays using electronic hybridization. The specific electronic hybridization procedures and probe attachment will vary slightly from device to device, and may be modified from the discussion below by one of ordinary skill in the biochemical arts. For the purposes of illustration, hybridization and detection procedures will be described with reference to the Nano-Chip™ electronic hybridization device, similar to that pictured in FIG. 2. However, other electronically addressable devices for microscale biochemical reactions may be utilized to carry out the methods of the invention.

Capture probes are immobilized via interaction with a permeation layer on the electronic microarray surface, as described in U.S. Pat. No. 5,605,662 , incorporated fully herein by reference. The stable interaction of the probes may be accomplished by a variety of different methodologies including, but not limited to, streptavidin-biotin interactions in which the capture probes contain a biotin moiety at the 5' end and streptavidin is incorporated within the permeation layer.

Biotinylated capture probes specific to each target of interest are immobilized at different position, or test site, on the microarray using electric field transport (i.e., electronically addressed to the test sites). When primer-extension detection methods will be used to quantify hybridized amplicons, the biotin label should not be on the 3' phosphate of the capture probe, so that the phosphate is available for extension in the polymerase reaction. In embodiments where Type IIs endonuclease shortening is used, these capture probes are designed to be complementary to the target sequence that is between the type IIs restriction endonuclease recognition site and the type IIs restriction endonuclease cleavage site. The capture probes may contain additional target-specific sequence including the type IIs restriction endonuclease recognition sequence and upstream sequence. In embodiments where bookending primers are used, capture probes are designed to hybridize to a region flanked by the binding sites for the chimeric oligonucleotide and the gene-specific oligonucleotide used to fill in single-stranded amplified products and/or generate cDNA. Generally the capture probes will comprise about 18 to about 30 bases, although shorter or longer capture probes may be utilized with electronic hybridization procedures. Capture probes may include non-amplicon-complementary sequences for use in zip-code addressing of the probes, or for other purposes (e.g., restriction endonuclease sites for selective cleavage).

In a preferred embodiment, a capture probe complementary to a control sequence is addressed to one or more location(s) on the microarray. This control sequence may be a housekeeping gene that is expressed at similar levels under the different conditions being examined, or may be an exogenous sequence which is added to the sample nucleic acid mixture prior to or after amplification. In a preferred embodiment, the capture probe complementary to the housekeeping gene is combined with each target-specific capture probe, and the two capture probes are co-addressed to a given position(s) on the microarray. This embodiment allows normalization within each position of the microarray, allowing better quantitative results. The microfluidics utilized to feed a sample nucleic acid solution introduce variations in exposure of each individual test site to the sample nucleic acid solution because of flow patterns, pooling, etc. Thus, the use of an internal control probe at each test site position allows for the normalization of assay data for each individual test site microenvironment.

The pool of shortened amplicons (in vitro transcribed target template(s), or cDNA copies thereof) is subsequently electronically hybridized to the immobilized capture probes. Because sites on the array are electronically controlled, hybridization can be restricted to a subset of locations within the microarray. Thus, different shortened amplicon pools, derived from different samples, can be analyzed on the same microarray. For these experiments, one pool of shortened amplicons from a given condition, cell type, or other source is injected into the electronic hybridization device, electronically transported to a subset of locations within the microarray, and allowed to hybridize with specific immobilized capture probes at those locations. Subsequently, this target pool is removed, unbound nucleic acids are washed away, and a second pool of targets from a different condition, cell type, or other source is injected and electronically transported to a distinct subset of locations within the microarray that contains the same immobilized target-specific capture probes. This second target pool is allowed to hybridize and unbound material is removed by washing. Subsequently, hybridized target species are detected by one of a variety of reporting methodologies.

This procedure, which allows direct analysis of a set of targets from different target samples on the same microarray, represents a particular strength of electronic hybridization in the area of gene expression profiling. Using the methods of the invention, it is easy for one of skill in the art to assay at least two, at least ten, and even fifty or more samples in a single experiment. The results of this process are illustrated in FIG. 6, which shows the hybridization of two groups of mRNA amplicons on the same chip: one sample was isolated from monocytes which have been treated with lipopolysaccharide, and the other sample was isolated from untreated monocytes. Alternatively, different electronic microarrays can be used to analyze expression patterns in different amplicon samples.

Detection of Hybridized Amplicons on Electronic Microarrays

Following electronic hybridization of target(s) to immobilized capture probes, the bound target(s) may be detected by several means, including include all commonly employed nucleic acid hybridization interaction detection methods such as primer extension labeling, amplicon labeling preferably through labeled sequence-specific primers), reporter probe detection, and even intercalating dyes. The detectable moiety in these labeling methods may be a fluorophore, chemiluminescent, colorigenic, or other detectable moiety. Fluorophore moiety labels are preferred for use in the present invention because of their widespread availability and relative ease of use.

In one preferred embodiment, the hybridized amplicons are detected by hybridization of a reporter species, such as a distinct target-specific oligonucleotide, that is labeled such that a detectable signal is produced, either directly or in combined action with an additional component(s) of a signal-producing system. An example of a directly detectable label is a fluorescent moiety that is present on the reporter, including, but not limited to, bodipy dyes such as Bodipy Texas Red and cyanine dyes such as Cy3 and Cy5. In a preferred embodiment in which the capture probe complementary to the housekeeping gene, or the control, is combined with each target-specific capture probe and co-addressed to a given position on the microarray, the reporter for the said housekeeping gene is labeled with a fluorophore emitting at one wavelength, while the reporters for the amplicons of the genes of interest are labeled with a different fluorophore that emits at least one other wavelength. Analysis of signal generated at each wavelength allows detection of all species hybridized on the microarray and subsequent normalization using the expression data from the housekeeping gene.

In another preferred embodiment, detection of at least a portion of the hybridized amplicons of the genes of interest is accomplished by enzymatic reporting. In this variation, after electronic hybridization, the microarray is incubated with reagents that allow primer extension of the capture probe using the bound RNA or cDNA amplicon target(s) as a template. For RNA targets, the extension is performed using an enzyme with reverse transcriptase activity, e.g. Superscript® reverse transcriptase, that uses RNA-DNA hybrids, but not RNA-RNA or DNA-DNA hybrids, as a template. Utilization of such enzyme will reduce non-specific signal that otherwise may be produced from extension of self-annealed regions of either capture probes or target molecules. For cDNA targets, an enzyme with DNA polymerase activity is used. In either case, one or more of the nucleotides present in the reaction will be labeled. The nucleotide species may be either deoxynucleotide(s) or dideoxynucleotide(s) and may be labeled with any detectable moiety, usually a fluorescent moiety. Preferred fluorescent moieties for use in the primer extension methods of the invention include cyanine dyes, e.g. Cy5 and Cy3, and other fluorescent dyes such as Bodipy Texas Red, rhodamine, fluorescein, and cumarin. Incorporation of the labeled nucleotide(s) into the extended capture probe will allow target-specific hybridization of the amplicons to be detected as a fluorescent signal at the individual test sites in the array. Other reagents included in the reaction include buffer medium for optimal enzymatic activity; such medium is commercially available and known to those of skill in the art.

In embodiments where the capture probe for the housekeeping target is co-addressed with target-specific capture probes, these two species must be differentiated at the reporting step. In one variation, a reporter specific for the housekeeping gene is allowed to hybridize prior to, concurrent with, or after the primer extension of capture probes specific for the genes of interest. The reporter is modified (e.g., by phosphoramidite chemistry or other means known in the art) at the 3' end to prevent extension of the reporter species during the primer extension reaction. The housekeeping gene-specific reporter is labeled such that the signal from the hybridized reporter can be distinguished from the signal generated from the extended target-specific capture probes, e.g. the reporter is labeled with Cy3 and the labeled NTP(s) used in the primer extension reaction is labeled with Cy5. In a preferred variation, the capture probe for the housekeeping gene is also modified at the 3' end, e.g. with an amino-blocking group, to prevent primer extension. Use of a blocked capture probe allows simultaneous hybridization of the reporter complementary to the housekeeping gene and primer extension of the target-specific capture probes, since the blocked capture probe hybridized to the housekeeping gene will not be extended.

The hybridization patterns are analyzed after signal detection. The signal generated by the housekeeping gene, which is expressed at equivalent levels in the different samples tested, is used to normalize differences in total nucleic acid concentration, electronic transport, and electronic hybridization efficiencies between samples, and to account for micro-environmental variations between test sites. Differences in intensities in the target amplicon signals after normalization is an indication of altered expression levels in the original mRNA in the sample nucleic acids under the conditions examined.

Applications of the Present Methods

The methods of the present invention may be readily applied to a wide variety of gene expression experimental models for use in studying, for example, disease and oncogenesis, physio-chemical cellular responses to stimuli, and cell growth and differentiation. The disclosed methods are ideal for these applications because of their speed, reproducibility, and flexibility as to the number, kind, and concentration of gene probes used in the hybridization experiment. As generally outlined below, the disclosed methods can greatly increase the ease and rapidity of common expression experiments.

For example, the methods of the present invention may easily be used to titrate the amount of amplified mRNA present in a sample. As illustrated in FIG. 5, a sample of amplified nucleic acids may be serially diluted. Each dilution may then be specifically hybridized with a subset of electronically activated test sites on a NanoChip™ device. By producing a concentration curve from the serial dilution data, the original concentration of the amplified mRNA sequence in the sample may be determined. If a specific amount of control sequence is added to the sample prior to amplification for use as a control, this amplified mRNA concentration may also be utilized to determine the original mRNA concentration in the sample. Thus, the methods of the invention may be used to obtain absolute quantitative measurements, as well as relative quantitative measurements of gene expression.

The methods of the present invention may also be used advantageously to compare, side by side, the expression levels of mRNA in a cell type that has undergone two different physical or chemical stimuli. For instance, in Example 5, the expression levels of four genes in monocyte cells which were treated with LPS (lipopolysaccharide) or untreated (control) were examined. As shown in FIG. 6, a marked change in several genes was observed between the LPS treated monocytes and the untreated monocytes. Similar experiments may easily be devised by those of skill in the art for screening potential chemical inducers or repressors of gene expression for use in combinatorial-library high-throughput drug discovery, while monitoring the effects of the compound on non-target gene expression pathways to minimize side effects.

Because of the flexibility of being able to perform multiple sample tests on the same electronically assisted hybridization device, the specific format of an assay may also be easily changed to suit new directions in a particular research project. For instance, a researcher may initially use a 100 test site NanoChip™ to screen 50 different genes in two samples from a cell line that has and has not been exposed to a chemical agent. Upon identifying 5 genes of particular interest, the researcher may then strip off the old probes from the streptavidin permeation layer, reconfigure the 100 test sites with using just 5 of the original 50 probes, and verify the result with a larger sample set of 5 controls and 15 stimulated cell samples, using 3 groups of cells stimulated with different concentrations of the chemical agent. Once an apparent rough critical concentration of chemical agent has been identified, four cell samples may be stimulated with concentrations of the agent centered around the rough critical concentration. The amount of amplified mRNA produced at each concentration may then be determined from four serial dilutions of each sample, utilizing the NanoChip™ as configured for screening the 20 samples above. As each screening step may be accomplished in 10 minutes to an hour, the entire project may be completed in a manner of days utilizing the methods of the present invention, depending on the stimulation period allotted for the cell samples The following examples are offered to further illustrate the various aspects of the present invention, and are not meant to limit the invention in any fashion. Based on these examples, and the preceding discussion of the embodiments and uses of the invention, several variations of the invention will become apparent to one of ordinary skill in the art. Such self-evident alterations are also considered to be within the scope of the present invention.

EXAMPLES

Example 1

General Protocol for Gene Expression Monitoring with Shortened Amplicons

A. cDNA synthesis.

Total RNA (5 $\mu$g) or poly(A$^+$) RNA(0.5 $\mu$g) was used as template in cDNA synthesis reactions with Superscript™ II RNase H_ Reverse Transcriptase (Life Technologies, Rockville, Md.) per manufacturer's instructions, with the inclusion of 10 U RNase Inhibitor (Roche Diagnostics, Mannheim, Germany). Synthesis was primed with either 500 ng oligo(dT)$_{12-18}$ (Life Technologies), or with oligo (dT)$_{17}$V (where V=A, G, or C), or with an oligo (dT)$_{18}$T$_{mod}$N$_3$) containing a non-replicable 1,3-propane diol moiety on the fourth base from the 3' end (U.S. Pat. No. 6027923). When an exogenous target gene was used as a control, 100–500 pg poly(A$^+$) RNA for the target was included in this initial cDNA synthesis reaction.

B. Linear amplification using DNA polymerase.

One-fourth to one-half of the cDNA synthesis reactions was used in Vent$_R$®(exo$^{31}$) DNA polymerase (New England Biolabs, Beverly, Mass.) mediated primer extension reactions. 1×Thermopol Buffer (New England Biolabs), 200 nM each dNTP (Roche Molecular Biochemicals, Indianapolis, Ind.), 50 nM each biotinylated chimeric T7-target specific oligonucleotide [See Table 2], and 0.04 U/ml reaction Vent$_R$ (exo$^-$) DNA polymerase were used. Final Mg$^{++}$ concentration was generally 2.3 mM, but was occasionally adjusted to as much as 4.6 mM. Chimeric primers for one to nine specific targets were added, in addition to a chimeric oligonucleotide specific for the internal (exogenous or endogenous) control. Samples were denatured at 95° C. 10 min, then cycled 30–50 times at (95° C. 30 sec, 50–60° C. 60 sec, 72° C. 60 sec). After the last cycle, samples were held at 72° C. for 5 min. 50 ng random hexamer primers. (Life Technologies) or 200 nM target-specific oligonucleotide(s) were added and annealed to the amplified targets at 42° C., 10 min. Annealed primers were extended by increasing the temperature to 70° C., 10 min.

C. Binding of amplified targets to streptavidin-coated magnetic beads and in vitro transcription reactions.

Amplified targets were isolated from other components of the amplification reaction mixture by binding to streptavidin-coated magnetic beads (Dynal®, Oslo, Norway) 30–60 min at 37° C. with occasional agitation. Beads were then isolated on a magnetic separator (Dynal) and the bound target was used as template for in vitro transcription reactions using the T7 MegaShortScript in vitro transcription kit (Ambion, Inc., Austin, Tex.). Reactions were incubated as per manufacturer's instructions 2–4 hr at 37° C. Transcribed RNA was purified from excess NTPs by isolation with Chromaspin-30 columns (Clontech, Palo Alto, Calif.) as per manufacturer's instructions. The RNA targets were used directly for analysis on microelectronic arrays, or used as template in a second cDNA synthesis reaction as described below.

D. Second round cDNA synthesis

20 µl of in vitro transcribed RNA was used as template in a second cDNA synthesis reaction. 50 ng random hexamer primers (Life Technologies) (sometimes used in multiplex analysis amplification) or 200 nM target-specific oligonucleotide(s) were annealed to RNA targets at 70° C. 10 min. 1×First strand buffer, 10 mM DTT, and 0.5 mM dNTPs (Roche Molecular Biochemicals, Indianapolis, Ind.) were added; samples were incubated at 42° C. 2 min prior to addition of 300 U Superscript™ II RNase H⁻ reverse transcriptase (Life Technologies). Reactions were incubated at 42° C. 50–75 min. 1 µg RNaseA (Ambion, Inc.) and 1 U RnaseH (Life Technologies) were added per reaction and samples were incubated at 37° C. 10 min. Samples were then desalted on either Chromaspin-30 columns (Clontech) or Bio-Spin 6 columns (Bio-Rad Laboratories, Hercules, Calif.) and used on microelectronic arrays. N.B. When restriction digestion is done, we use RNA target, we don't convert it into cDNA. The choice of random hexamer v. gene specific oligo for cDNA synthesis is based on the advantage random hexamers provide in multiplexing experiments weighed against the possible reduction in amount of detectable cDNA generated.

E. Electronic capture addressing and target hybridization.

500 nM target-specific biotinylated capture oligonucleotide in 50 mM histidine was electronically addressed to specific sites on the NanoChip™, using the Nanogen Molecular Biology Workstation. Probes were transported using 2.0 V constant voltage for 1 minute; typically, 2–10 pads were addressed simultaneously. Unbound oligonucleotides were removed by washing with 50 mM histidine. When an internal control was included within the sample, 500 nM capture for this species was co-addressed with target-specific capture oligonucleotide; this internal control capture is blocked at the 3' end with an amino modifier to prevent extension in the subsequent reporting reaction.

RNA or cDNA targets in 50 mM histidine were heat-denatured by incubation at 95° C. 5 min and quick-chilled on ice. Targets were electronically hybridized to specific capture oligonucleotides using 2.0V for 2–3 min; typically, 2–10 sites on the array were addressed simultaneously. Unhybridized nucleic acids were removed by washing with 50 mM histidine.

F. Reporting

The internal control target is detected by hybridization with 0.5–1 µM 3' Cy3-labeled oligonucleotide that binds directly adjacent to the capture oligonucleotide; this reporter oligonucleotide can be included in the enzymatic reporting mixture. Targets of interest that are hybridized to capture oligonucleotides are detected by extension of the capture probes in the presence of Cy5-labeled dCTP. For RNA targets, after the final hybridization reaction and washing was completed, the NanoChip™ was incubated with 1×First strand buffer (Life Technologies); 10 mM DTT (Life Technologies); 0.25 mM each dATP, cGTP, and dTTP (Roche Molecular Biochemicals, Indianapolis, Ind.); 0.125 mM Cy5-dCTP (Amersham Pharmacia Biotech, Buckinhamshire, England); and 200 U Superscript™ II RNase H⁻ reverse transcriptase (Life Technologies) for 10 min at 37° C. For cDNA targets, the NanoChip was incubated in 50 mM NaPO₄ for 10 min at 37° C. prior to enzymatic extension of the capture oligonucleotide(s). Reporting of hybridized cDNA targets was performed as described for RNA targets, except that 1×Second strand buffer (Life Technologies) and 20 U DNA polymerase I (Life Technologies) were used in place of First strand buffer and reverse transcriptase. Following the enzymatic extension reaction, NanoChip™ were washed with 50 mM NaPO₄. Due to the high salt content of the enzymatic reporting mixture, the included Cy-3 labeled internal control probe hybridizes to the housekeeping sequence fairly rapidly at the 37° C. incubation temperature. Fluorescence from the Cy3-labeled internal control reporter and from the incorporated Cy5-dCTP was detected on the Nanogen Molecular Biology Workstation.

For quantitation of targets, the signal from the Cy3 labeled internal (exogenous or endogenous) control gene, the expression of which is not expected to change under the conditions being examined, is equalized, and a normalization factor is thus obtained. Target-specific signal (Cy 5) is then adjusted by this normalization factor. The amount of change in target gene expression level under the experimental condition may then be determined by comparing these adjusted hybridization/fluorescence values.

Example 2

Enzymatic-mediated Shortening of Targets cDNA synthesis and amplification were as described above. Following Vent$_R$®(exo⁻) DNA polymerase-mediated amplification and fill-in reactions, the targets were enzymatically shortened by digestion with the type IIs restriction endonuclease BpmI, utilizing a BpmI recognition site in the endogenous sequence of IL6, TGFβ1, and p53 and chimeric primer altered sites in COX1 and GAPDH, as described in Example 4. Digestion was performed at 37° C. for 1.5–2 h. Streptavidin-coated magnetic beads were then added and incubation was continued at 37° C. for an additional 30–60 min. The bead-bound targets were used in in vitro transcription reactions as described above, and RNA targets were analyzed on NanoChip™ microarrays.

Example 3

Re-use of Targets Bound to Streptavidin-coated Magnetic Beads for Multiple in vitro Transcription Reactions.

After the initial cDNA synthesis reaction and Vent$_R$® (exo⁻) DNA polymerase mediated amplification, as described above, double stranded target(s) are immobilized on streptavidin-coated magnetic beads via the biotin moiety introduced by the chimeric T7 RNA polymerase recognition site-gene specific oligonucleotide. These targets are then used as templates in in vitro transcription reactions, as described above. Following in vitro transcription, the bead-bound target can be stored at 4° C. and re-used in subsequent in vitro transcription reactions. This aspect of the protocol allows re-analysis of targets of interest from a given sample pool without having to obtain more of the initial cellular RNA.

Figure 3:
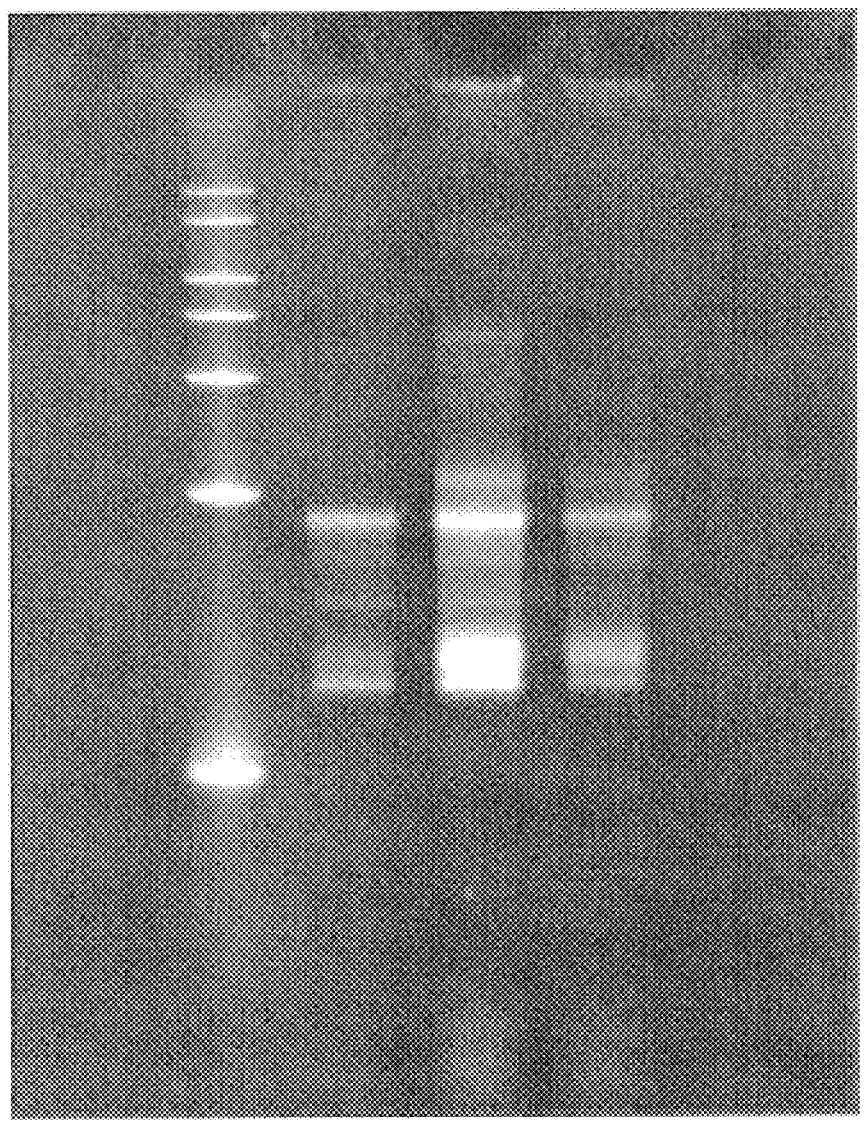
FIG. 3: Shown are the agarose gel electrophoresis-separated RNA products of a $1^{st}$, $2^{nd}$, and $3^{rd}$ round of in vitro transcription from the same double stranded amplified cDNA library immobilized on magnetic streptavidin-coated beads. The far left lane contains a molecular size marker.

FIG. 3 demonstrates the results obtained when a single pool of bead-bound targets is utilized in three separate rounds of in vitro transcription. Note that, unexpectedly, the amount of transcript produced decreases only slightly between the first and third rounds of transcription, and the decrease in the amount of transcript is not significant between transcription rounds. Several additional rounds of in vitro transcription are possible, with a minimal iterative decrease in the amount of transcript produced.

Example 4
Demonstration of the Effect of Amplicon Size on Hybridization Efficiency in Electronic and Passive Hybridization Systems Cellular messenger RNA was isolated from cultured U937 monocyte cells (see Example 5) and reverse transcribed into cDNA with oligo(dT)$_{12-17}$. The hybridization of COX1, GAPDH, IL6, TGFβ1, and p53 amplicons of approximately 50, 100, 250, and 500 bases in size were determined utilizing both electronic (as described above) and passive hybridization procedures (outlined below), using a TPOX control for normalization of the hybridization values. One primer for each target contained the T7 RNA polymerase recognition site upstream of gene specific sequence; these primers were designed to incorporate a BpmI site at the 3' end. The other primers were designed to generate products that were 100 bp, 250 bp, or 500 bp in length. A portion of the 100 bp amplified target was digested with BpmI to generate 50 bp fragments. After amplification, similarly sized targets were pooled and used as template in in vitro transcription reactions with the T7 MegaScript or MegaShortScript kits (Ambion, Inc.). The different pools of RNA targets were then hybridized passively or electronically to microarray sites co-addressed with target-specific and control (TPOX)-specific capture oligonucleotides. Hybridized targets were detected by enzymatic extension of the hybridized capture oligonucleotides in the presence of Cy5-dCTP. In the case of the internal control TPOX, this reporter was labeled with Cy3;.

A) Exponential amplification of target sequences

For exponential amplification of cDNA, one-tenth (2 μl) of a standard cDNA synthesis reaction was utilized. Amplification was performed in the presence of 1×PCR buffer II (Perkin Elmer, Foster City, Calif.); 0.2 μM each primer; 200 μM dNTP mix; and 2.5 U AmpliTaq Gold (Perkin Elmer). cDNA was denatured at 95° C. 10 minutes, then amplified by cycling (95° C. 30 sec; 50–60° C. 60 sec; 72° C. 120 sec). Amplification reactions were generally performed for 25–30 cycles. The annealing temperature was chosen to be 5° C. lower than the Tm of the primers.

B) Passive hybridization of RNA targets 10 nM RNA targets were passively hybridized to capture-loaded microarrays by incubation in 4×SSC, 1×Denhard's , and 100 μg yeast tRNA. Hybridization was performed by placing the microarray on a moist piece of filter paper in a small petri dish. The dish was sealed with Parafilm (American National Can, Neenah, Wis.) and the microarray was incubated 14–16 hr at 37° C. The hybridization solution was subsequently removed and the unbound target removed by washing with 50 mM NaPO$_4$.

C) Passive hybridization of labeled reporter oligonucleotides

In the case where fluorescently labeled reporter oligonucleotides exclusively are used to detect target species on the microarray, 1 μM each reporter species is passively hybridized to the immobilized target in 50 mM NaPO$_4$/500 mM NaCl. This hybridization reaction is performed at 23° C. for 5 min; unbound reporters are then removed by washing with 50 mM NaPO$_4$ prior to imaging of the microarray.

Figure 4:
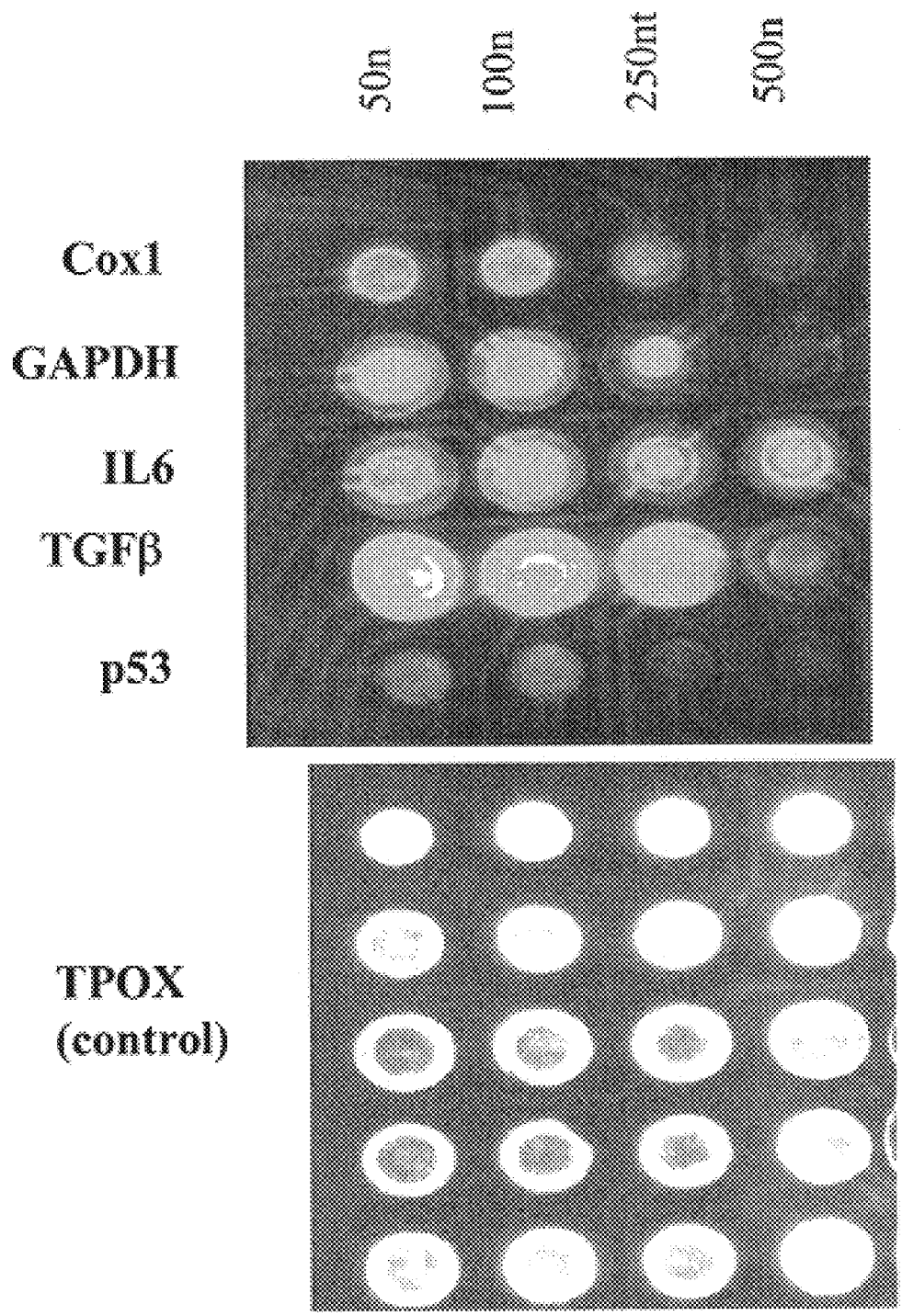
FIG. 4: Shown are grayscale hybridization fluorescence data for five separate gene probes, using 50, 100, 250, and 500 nucleotide amplicons. As can be seen from the best results were obtained using amplicons of around 100 bases in length.

The hybridizations utilized to generate the electronic hybridization data are shown in FIG. 4.

TABLE 1

Effect of target size on hybridization efficiency

| Target Gene: | 50 nt | 100 nt | 250 nt | 500 nt |
|---|---|---|---|---|
| ELECTRONIC HYBRIDIZATION: (After 2–3 minutes) | | | | |
| COX2 | 36.6 | 45.8 | 21.0 | 4.62 |
| GAPDH | 77.2 | 95.0 | 39.5 | 2.22 |
| IL6 | 46.9 | 69.2 | 47.3 | 49.2 |
| TGFβ | 206 | 187 | 131 | 16.9 |
| p53 | 17.5 | 19.4 | 1.65 | ND |
| PASSIVE HYBRIDIZATION: (After 14–16 hours) | | | | |
| COX1 | 34.4 | 28.0 | 6.06 | 5.51 |
| GAPDH | 68.1 | 75.0 | 6.89 | 2.20 |
| IL6 | 71.3 | 26.4 | 12.9 | 6.91 |
| TGFβ1 | 150 | 150 | 38.2 | 6.86 |
| p53 | 23.0 | 14.6 | 6.17 | 6.76 |

These numbers represent fluorescence units

As can be seen from the above data, the length of the amplicons used in the hybridization procedure had a marked effect on hybridization efficiency.

Example 5
Demonstration of Gene Expression Monitoring in LPS Stimulated Monocyte Cells The monocytic cell line U937 was cultured to 4×10$^7$ cells/75 cm$^2$ flask in RPMI media (American Type Culture Collection, Manassas Va.) containing 10% Fetal Bovine Serum (American Type Culture Collection) and 200 units/g/ml penicillin/streptomycin (Life Technologies) in two or more flasks. Cells were collected and resuspended in either RPMI/FBS/antibiotics or in RPMI/FBS/antibiotics+phorbol myristate acid (Life Technologies) at a final concentration of 10 ng/ml. 72 h after PMA treatment, cells were collected and resuspended in RPMI media containing FBS and antibiotics; PMA-treated cells were induced by treatment with 500 ng/ml lipopolysaccharide (Sigma, St. Louis, Mo.). Cells were harvested 6 h after addition of LPS. Uninduced cells that had been maintained in RPMI/FBS/antibiotic medium were also collected ("Uninduced"). Untreated and treated cells were snap frozen in liquid nitrogen until needed for mRNA isolation.

mRNA isolation was performed with the Poly(A) Pure Isolation kit (Ambion, Inc.). Cellular poly(A$^+$) RNA was isolated and cDNA was generated using the propane diol-modified oligo dT primer. Limited amplification reactions were performed in duplex reactions as follows: the biotinylated chimeric T7-gene specific oligonucleotides for Interleukin I beta (IL1) and Transforming Growth Factor beta-2 (TGFβ2) were used in one amplification reaction; and the biotinylated chimeric T7-gene specific oligonucleotides for Interleukin 6 (IL6) and c-jun were used in a second amplification reaction. Single stranded targets were filled in by addition of gene specific oligonucleotides and used in in vitro transcription reactions. The RNA generated was used as template for second cDNA syntheses. Electronic capture addressing, target hybridization, and enzymatic extension with DNA polymerase were carried out as described in Example 1.

Figure 7:
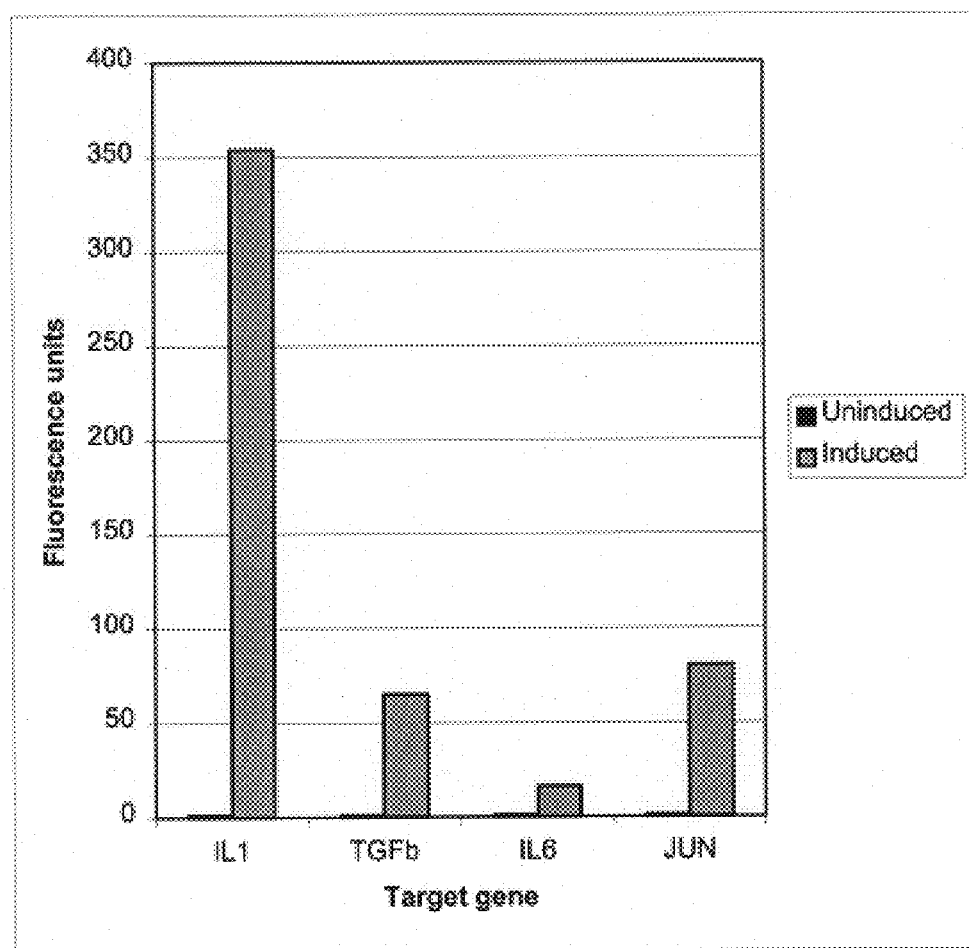
FIG. 7: A graphical illustration of the results shown in FIG. 6.

The hybridization results of the experiment are shown in FIG. 6, and graphically represented in FIG. 7. cNS represents a non-specific biotinylated oligonucleotide that does not contain sequence complimentary to any of the amplified targets. As shown, the addition of LPS to the monocyte cell culture provoked dramatically increased mRNA expression for IL1, moderately increased expression of TGFβ2 and c-jun message, and minimally increased expression of IL6. Thus, as illustrated, altered expression of genes between two sample cell populations can be easily monitored using the methods of the present invention.

Example 6
Demonstration of Serial Dilution and Quantitative Methods Utilizing the NanoChip™ Electronic Hybridization Device
A) Detection of Serially Diluted Short RNA Targets on the NanoChip™

Figure 5A:
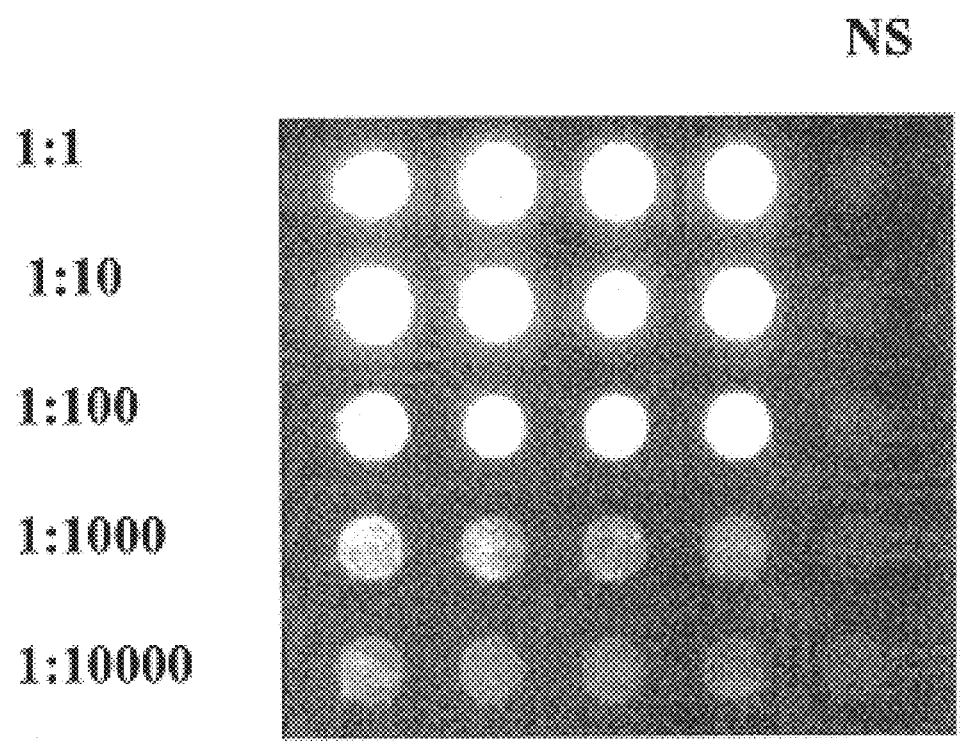
FIG. 5a: Shown are grayscale hybridization fluorescence data for serial dilutions of amplified sample plasmid nucleic acids, hybridized to a β-la capture probe. NS denotes no capture sequence attached to the test sites in the far right column. Note the reproducibility of the hybridization signal across the rows of the electronic array.

The β-la target gene was amplified from plasmid DNA using chimeric gene specific oligonucleotides, as described above. The 5' primer (pT7 Amp.s1) contains a T7 RNA polymerase recognition sequence upstream of gene specific sequence; the 3' primer contains a poly(dT) tract downstream of gene specific sequence. This PCR product, representing the full-length β-la gene, was used as template in in vitro transcription reactions with the T7 Megascript kit per manufacturer's instructions (Ambion, Inc.). The target was reverse transcribed to generate cDNA, and the cDNA product was used in a Vent$_R$® (exo⁻) DNA polymerase-mediated amplification reaction with a second, internal chimeric T7 RNA polymerase recognition site/gene-specific oligonucleotide (pT7AmpBpm.s1). The amplified target was enzymatically digested with BpmI and used in a second in vitro transcription reaction using the T7 MegaShortScript kit (Ambion, Inc.). The resulting short RNA target was serially diluted as indicated and electronically hybridized to a β-la specific capture oligonucleotide. The electronic hybridization data is shown in FIG. 5a.

B) Detection of Exogenous Target in a Pool of Cellular RNA

Figure 5B:
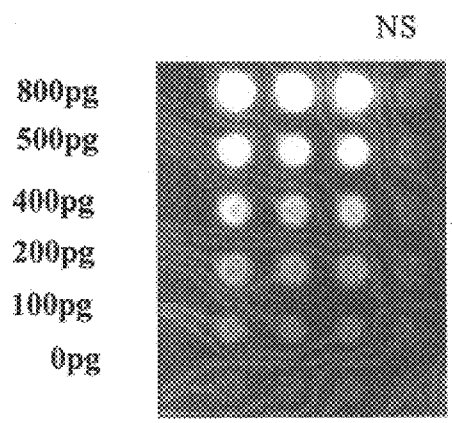
FIGS. 5b & 5c: Shown are grayscale hybridization fluorescence data for defined amounts of sample nucleic acid sequence, and a graphical representation of a concentration curve derived from these data.
Figure 5C:
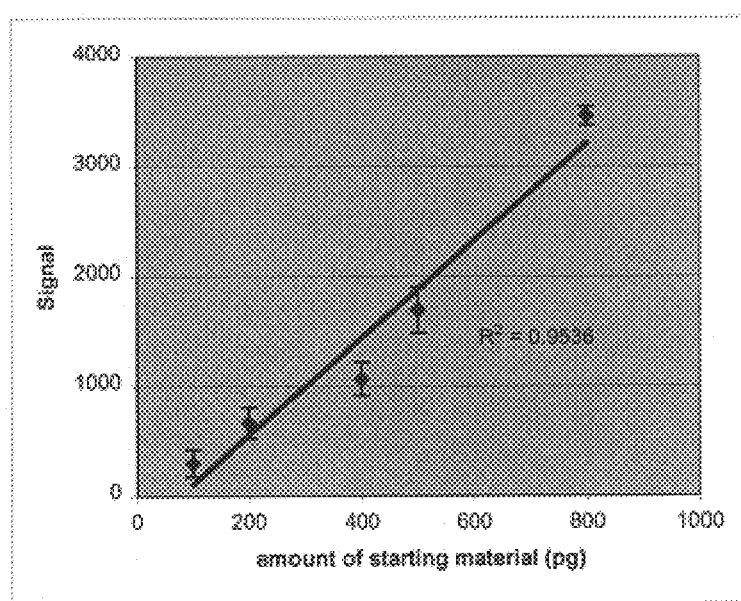

The full length β-la target was generated as described above. This RNA was added in defined amounts (0 to 800 pg) to 250 ng cellular messenger RNA. The entire pool of RNA was then reverse transcribed into cDNA, and the β-la target was amplified in a Vent® (exo⁻) DNA polymerase-mediated amplification reaction. The amplified target was enzymatically digested with BpmI and used in a second in vitro transcription reaction using the T7 MegaShortScript kit (Ambion, Inc.). The resulting short RNA target was electronically hybridized to a β-la specific capture oligonucleotide. The hybridization data is shown in FIG. 5b, and graphically represented in FIG. 5c.

TABLE 2

Oligonucleotides Used in the Above Experimental Procedures, Organized by Target Gene

| Target Gene | Primer name and description | Primer sequence |
| --- | --- | --- |
| Angiotensinogen | bAt7AngBpm.s1-biotinylated chimeric T7 promoter/gene specific oligonucleotide | BiotinTAATACGACTCACTATAGG GAGACACAGAACTGGATGTTGC TGCTGGAG [SEQ.ID NO.1] |
| Angiotensinogen | cAng.a1-capture for RNA | BiotinCATGAACCTGTCAATCUCT [SEQ. ID NO.2] |
| Angiotensinogen | pAng.a1-3' gene specific primer | GGAAGGTGCCCATGCCAGAGA [SEQ. ID NO.3] |
| Cathepsin G | bAt7CathBpm.s1 - biotinylated chimeric T7 promoter/gene specific oligonucleotide | BiotinTAATACGACTCACTATAGG GAGAGCTGCCTTCAAGGGGGAT TCTGGAG [SEQ. ID NO.4] |
| Cathepsin G | pCath.a1-3' gene specific primer | AGCTTCTCATTGTTGTCCTTATC C [SEQ. ID NO.5] |
| Cathepsin G | cCath.a1-capture for RNA | BiotinTGTTACACAGCAGGGGGC CT [SEQ. ID NO.6] |
| c-jun | bT7jun.s1-biotinylated chimeric T7 promoter/gene specific oligonucleotide | BiotinTAATACGACTCACTATAGG GAGACGGCCAACATGCTCAGGG AACAGGT [SEQ. ID NO.7] |
| c-jun | cjun.s1-capture for cDNA | BiotinCAAACATTTTGAAGAGAGA CCGTCG [SEQ. ID NO.8] |
| c-jun | pjun.a1-3' gene specific primer | TTTTTCTTCGTTGCCCCTCAGCC [SEQ. ID NO.9] |
| COX1 | pcox1.as.3-gene specific primer for generation of 500 bp fragment | TGCCCAGGATTGATTCACAGG [SEQ. ID NO.10] |
| COX1 | pcox1.as.2-gene specific primer for generation of 250 bp fragment | AGGCCAGAAGGAATGATGGG [SEQ. ID NO.11] |
| COX1 | pcox1.as.1-gene specific primer for generation of 100 bp fragment | CTAAGCCCAAAGTGTGGATC [SEQ. ID NO.12] |
| COX1 | T7.cox1.s-chimeric T7/gene specific oligonucleotide | GAAATTAATACGACTCACTATAG GGAGAACCCTTTTCTCAGGACCT CTGGAGG [SEQ. ID NO.13] |
| COX1 | cCOX1bpm.a1-capture for RNA | BiotinACAGAGGTCCTGAGAAAAG GGTCT [SEQ. ID NO.14] |

TABLE 2-continued

Oligonucleotides Used in the Above Experimental Procedures, Organized by Target Gene

| Target Gene | Primer name and description | Primer sequence |
|---|---|---|
| COX2 | bAt7COX2bpm.s2-biotinylated chimeric T7 promoter/gene specific oligonucleotide | BiotinTAATACGACTCACTATAGG GAGACTATGAATCATTTGAAGAA CTTACTGGAG [SEQ. ID NO.15] |
| COX2 | cCOX2.a2-capture for RNA | BiotinCTGCAGACATTTCCTTTTCT [SEQ. ID NO.16] |
| COX2 | pCOX2.a2-3' gene specific primer | GCATCTGGCCGAGGCTTTTCTAC [SEQ.ID NO.17] |
| GAPDH | pGAPs.2-3' gene specific primer for generation of 500 bp fragment | GTTCGACAGTCAGCCGCATCTTC [SEQ. ID NO.18] |
| GAPDH | pGAPs.3-gene specific primer for generation of 100 bp fragment | TGATGCCCCCATGTTCGTCATGG [SEQ. ID NO.19] |
| GAPDH | pGAPs.4-gene specific primer for generation of 250 bp fragment | CTTCCAGGAGCGAGATCCCTCC [SEQ. ID NO.20] |
| GAPDH | T7GAPbpm.a1-chimeric T7/gene specific oligonucleotide | GTAATACGACTCACTATAGGGCG GGGTGCTAAGCAGTTGGTGGTG CTGGAG [SEQ. ID NO.21] |
| GAPDH | cGAPbpm.s1-capture for aRNA | BiotinCAGCCTCAAGATCATCAGC AATGCCT [SEQ. ID NO.22] |
| GAPDH | bAt7GAPbpm.s2-biotinylated chimeric T7 promoter/gene specific oligonucleotide | BiotinTAATACGACTCACTATAGG GAGACTCAAGGGCATCCTGGGC TACACTGGAGCAC [SEQ. ID NO. 23] |
| GAPDH | pGAPDH.a6-3' gene specific primer | GAGGTCCACCACCCTGTTGCTG TAG [SEQ. ID NO.24] |
| GAPDH | cGAPbpm.a2-capture for RNA | BiotinGTTGAAGTCAGAGGAGACC ACCTGGTGCT [SEQ. ID NO.25] |
| HMG-17 | bAt7HMG17Bpm.s1-biotinylated chimeric T7 promoter/gene specific oligonucleotide | BiotinTAATACGACTCACTATAGG GAGAGGAATAACCCTGCAGAAA CTGGAG [SEQ. ID NO.26] |
| HMG-17 | pHMG17.a1-3' gene specific primer | CCCTTCCCCCAAAAACAACAATG A [SEQ. ID NO.27] |
| HMG-17 | cHMG17.al-capture for RNA | BiotinCCTGGTCTGTTTTGGCATC T [SEQ. ID NO.28] |
| Interleukin 6 | pIL6s.4-gene specific primer for generation of 500 bp fragment | ATTCTGCCCTCGAGCCCACCGG G [SEQ. ID NO.29] |
| Interleukin 6 | pIL6S.3-gene specific primer for generation of 250bp fragment | CAAACAAATTCGGTACATCCTCG [SEQ. ID NO.30] |
| Interleukin 6 | pIL6S.2-gene specific primer for generation of 100 bp fragment | TGGATTCAATGAGGAGACTTGCC [SEQ. ID NO.31] |
| Interleukin 6 | T7IL6bpm.al-chimeric T7/gene specific oligonucleotide | GTAATACGACTCACTATAGGGCG CCTCACTACTCTCAAATCTGTTC TGGAG [SEQ. ID NO.32] |
| Interleukin 6 | cIL6bpm.s1-capture for aRNA | BiotinGGAGTTTGAGGTATACCTA GAGTACCT [SEQ. ID NO.33] |
| Interleukin 6 | bT7IL6.s1-biotinylated chimeric T7 promoter/gene specific oligonucleotide | BiotinTAATACGACTCACTATAGG GAGACCTGAGGGCTCTTCGGCA AATGTAG [SEQ. ID NO.34] |
| Interleukin 6 | cIL6.s1-capture for cDNA | BiotinAATGGGCATTCCTTCTTCT GGTCAG [SEQ. ID NO.35] |
| Interleukin 6 | pII6.a1-3' gene specific primer | GAACAACATAAGTTCTGTGCCCA GTG [SEQ. ID NO.36] |
| Interleukin 1 beta | bT7IL1.s1-biotinylated chimeric T7 promoter/gene specific oligonucleotide | BiotinTAATACGACTCACTATAGG GAGACAGAAAACATGCCCGTCTT CCTGG [SEQ. ID NO.37] |
| Interleukin 1 beta | cIL1.s1-capture for cDNA | BiotingGCGGCCAGGATATAACTGA CTTCAC [SEQ. ID NO.38] |
| Interleukin 1 beta | pII1.a1-3' gene specific primer | TCCACATTCAGCACAGGACTCTC TG [SEQ. ID NO.39] |
| LD78 | bAt7LD78Bpm.s1-biotinylated chimeric T7 promoter/gene specific oligonucleotide | BiotinTAATACGACTCACTATAGG GAGAAGTGACCTAGAGCTGAGT GCCTGGAG [SEQ. ID NO.40] |

TABLE 2-continued

Oligonucleotides Used in the Above Experimental Procedures, Organized by Target Gene

| Target Gene | Primer name and description | Primer sequence |
|---|---|---|
| LD78 | pLD78.a1-3' gene specific primer | CTCTCAGAGCAAACAATCACAAA CACAC [SEQ. ID NO.41] |
| LD78 | cLD78.a1-capture for RNA | BiotinTCGAAGCTTCTGGACCCCT [SEQ. ID NO.42] |
| Osteopontin | bAt7OstBpm.s1-biotinylated chimeric T7 promoter/gene specific oligonucleotide | BiotinTAATACGACTCACTATAGG GAGAGAGGTGATAGTGTGGTTT ATGGACTGGAG [SEQ. ID NO.43) |
| Osteopontin | pOst.a1-3' gene specific primer | CAACGGGGATGGCCTTGTATGC [SEQ. ID NO.44] |
| Osteopontin | cOst.a1-capture for RNA | BiotinAACTTCTTAGATTTTGACCT [SEQ. ID NO.45] |
| p53 | pp53s.3-gene specific primer for generation of 500 bp fragment | ACAGAAACACTTTTCGACATAG [SEQ. ID NO.46] |
| p53 | pp53.s1-gene specific primer for generation of 250 bp fragment | AAAGGGGAGCCTCACCACGAGC [SEQ. ID NO.47] |
| p53 | pp53.s1-gene specific primer for generation of 100 bp fragment | CGTGAGCGCTTCGAGATGTTCC [SEQ. ID NO.48] |
| p53 | T7p53bpm.a1-chimeric T7/gene specific oligonucleotide | GTAATACGACTCACTATAGGGCG ACCCTTTTTGGACTTCAGGTGGC TGGAG [SEQ. ID NO.49] |
| p53 | cp53bpm.s1-capture for aRNA | BiotinGAGCCAGGGGGAGCAGG GCTCACT [SEQ. ID NO.50] |
| TGFβ1 | pTGFb1S.3-gene specific primer for generation of 500 bp fragment | GGGATAACACACTGCAAGTGGA C [SEQ. ID NO.51] |
| TGFβ1 | pTGFb1s.2-gene specific primer for generation of 250 bp fragment | CCACGAGCCCAAGGGCTACCAT GC [SEQ. ID NO.52] |
| TGFβ1 | pTGFb1.s1-gene specific primer for generation of 100 bp fragment | CGCTGGAGCCGCTGCCCATCGT GTA [SEQ. ID NO.53] |
| TGFβ1 | T7TGFb1bpm.a1-chimeric T7/gene specific oligonucleotide | GTAATACGACTCACTATAGGGCG GGCGGGACCTCAGCTGCACTTG CTGGAG [SEQ. ID NO.54] |
| TGFβ1 | cTGFb1bpm.s1-capture for aRNA | BiotinCAGCTGTCCAACATGATCG TGCGCT [SEQ. ID NO.55] |
| TGFβ2 | bT7TGFb.s1-biotinylated chimeric T7 promoter/gene specific oligonucleotide | BiotinTAATACGACTCACTATAGG GAGACTCTGCCTCCTCCTGCCT GTCTGC [SEQ. ID NO.56] |
| TGFβ2 | cTGFb.s1-capture for cDNA | BiotinCGGCATCAAGGCACAGGG GACCAGT [SEQ. ID NO.57] |
| TGFβ2 | pTGFb.a1-3' gene specific primer | CTTCAACAGTGCCCAAGGTGCT CAA [SEQ. ID NO.58) |
| TPOX | TPOX9C-biotinylated synthetic target | BiotinTTAGGGAACCCTCACTGAA TGAATGAATGAATGAATGAATGA ATGAATG [SEQ. ID NO.59] |
| TPOX | TPOXcapcomp-Cy3 labeled reporter for TPOX9C | CATTCATTCATTCAGTGAGGGTT CC [SEQ. ID NO.60] |
| Vimentin | bAt7VimBpm.s2-biotinylated chimeric T7 promoter/gene specific oligonucleotide | BiotinTAATACGACTCACTATAGG GAGACATCGACAAGGTGCGCTT CCTGGAG [SEQ. ID NO.61] |
| Vimentin | pVim.a1-3' gene specific primer | CGCGGGCTTTGTCGTTGGTTAG [SEQ. ID NO.62] |
| Vimentin | cVim.a2-capture for RNA | BiotinCAGGATCTTATTCTGCTGC T [SEQ. ID NO.63] |
| β-Actin | bAt7Actin.s-biotinylated chimeric T7 promoter/gene specific oligonucleotide | BiotinTAATACGACTCACTATAGG GAGACCCCTTTTTGTCCCCCAAC TGGAGA [SEQ. ID NO.64] |
| β-Actin | cActin.a-capture for RNA | BiotinCCAAAAGCCTTCATACATC T [SEQ. ID NO.65] |
| β-Actin | pbAa.4-3' gene specific primer | AAGGTGTGCACTTTTATTCAACT GGTCTCAAG [SEQ. ID NO.66] |

TABLE 2-continued

Oligonucleotides Used in the Above Experimental Procedures, Organized by Target Gene

| Target Gene | Primer name and description | Primer sequence |
|---|---|---|
| β-Ia | pT7AmpBpm.s1-chimeric T7/gene specific oligonucleotide for generation of short RNA | TAATACGACTCACTATAGGCTGG CTGGTTTATTGCTGATAAATCTG GAG [SEQ. ID NO.67] |
| β-Ia | pAmp.a2-3' primer with poly(dT) tract | $T_{30}$CCAATGCTTAATCAGTGAGGC ACCTATCTC [SEQ. ID NO.68] |
| β-Ia | cAmp.a1-capture for RNA | biotin-CGAGACCCACGCTCACCGGCT [SEQ. ID NO.69] |
| β-Ia | pT7Amp.s1-chimeric T7/gene specific oligonucleotide for generation of full-length gene | TAATACGACTCACTATAGGGCAC CCAGAAACGCTGGTGAAAGTAA AAG (SEQ. ID NO.70] |
| β-Thromboglobulin-like protein gene | bAt7Throm.s1-biotinylated chimeric T7 promoter/gene specific oligonucleotide | BiotinTAATACGACTCACTATAGG GAGAGGAAAACTGGGTGCAGAG GGTTCTGGAG [SEQ. ID NO.71] |
| β-Thromboglobulin-like protein gene | pbThrom.a1-3' gene specific primer | GGCAACCCTACAACAGACCCAC AC [SEQ. ID NO.72] |
| β-Thromboglobulin-like protein gene | cbThrom.a1-capture for RNA | BiotinAGCCCTCTTCAAAAACTTCT [SEQ. ID NO.73] |

We claim:

1. A method of providing an internal control for an individual test site in a nucleic acid hybridization reaction assay to determine the presence of at least one nucleic acid sequence of interest in at least one nucleic acid containing sample, wherein the nucleic acid hybridization assay is performed on an electronically controlled microarray comprising at least two test sites, the method comprising:

(a) attaching a nucleic acid probe mix consisting of a first nucleic acid probe specific for a first internal control nucleic acid sequence known to be present in the sample, and a second nucleic acid probe specific for a second nucleic acid sequence of interest to a first test site on the electronically controlled microarray;

(b) attaching a mixed nucleic acid probe consisting of the first nucleic acid probe and a third nucleic acid probe specific for a third nucleic acid sequence of interest, wherein the third nucleic acid sequence of interest may be the same as or different than the second nucleic acid sequence of interest, to a second test site on the electronically controlled microarray;

(c) electronically hybridizing the sample nucleic acids from at least one sample to the nucleic acid probes on the first and second test sites;

(d) specifically detecting the extent of hybridization of the sample nucleic acids to the first nucleic acid probe at the first and second test sites;

(e) specifically detecting the extent of hybridization of the sample nucleic acids to the second and third nucleic acid probes at the first and second test sites;

(f) comparing the hybridization values obtained for the first nucleic acid probe at the first and second test sites to obtain a normalization factor; and (g) normalizing the hybridization values obtained in (e) for the second and third probes using the normalization factor obtained in (f).

2. The method of claim 1 wherein the first nucleic acid sequence is a sequence which encodes, or is complementary to a sequence which encodes, a housekeeping gene.

3. The method of claim 1 wherein the first nucleic acid sequence is an exogenous nucleic acid sequence which has been added to the sample.

4. The method of claim 1 wherein the specific detection in (d) is by detecting a labeled nucleotide which has been specifically incorporated by a nucleic acid polymerase reaction into the sample nucleic acids which contain the first nucleic acid sequence.

5. The method of claim 1, further comprising the step of electronically or passively hybridizing a first reporter nucleic acid comprising a detectable moiety specific for the first nucleic acid sequence to the sample nucleic acids which are hybridized to the first nucleic acid probe at the first and second test sites, wherein the specific detection in (d) is by detecting the detectable moiety.

6. The method of claim 1, further comprising the step of extending the first nucleic acid probe by utilizing the sample nucleic acids which have hybridized to the first nucleic acid probe as a template for a nucleic acid polymerase reaction, wherein the specific detection in (d) is by detecting a labeled nucleotide which has been incorporated into the extended first nucleic acid probe by the polymerase reaction.

7. The method of claim 6, wherein the second and third nucleic acid probes attached in (a) and (b) comprise a protecting group that prevents enzymatic extension of the probes.

8. The method of claim 1 wherein the specific detection in (e) is by detecting a labeled nucleotide which has been specifically incorporated by a nucleic acid polymerase reaction into the sample nucleic acids which contain the second and third nucleic acid sequences of interest.

9. The method of claim 1, further comprising the step of electronically or passively hybridizing one or more reporter nucleic acid probes comprising a detectable moiety to the sample nucleic acids which are hybridized to the second and third nucleic acid probes at the first and second test sites, wherein the reporter probes are specific for the second and third nucleic acid sequences of interest and wherein the specific detection in (e) is by detecting the detectable moiety.

10. The method of claim 1, further comprising the step of extending the second and third nucleic acid probes by utilizing the sample nucleic acids which have hybridized to the second nucleic acid probe as a template for a nucleic acid polymerase reaction, wherein the specific detection in (e) is by detecting a labeled nucleotide which has been incorporated into the extended second and third nucleic acid probes by the polymerase reaction.

11. The method of claim 10, wherein the first nucleic acid probes attached in (a) and (b) comprise a protecting group that prevents enzymatic extension of the probes.

12. The method of claim 1, wherein a first detectable moiety is detected in step (d), and a second detectable moiety is detected in step (e).

13. The method of claim 12 wherein the first and second detectable moieties are independently selected from the group consisting of fluorescent moieties, colorigenic moieties, chemiluminescent moieties, and affinity moieties.

14. The method of claim 13 wherein the first and second detectable moieties are fluorescent moieties.

* * * * *

SEQUENCE LISTING

<160> NUMBER OF SEQ ID NOS: 73

<210> SEQ ID NO 1
<211> LENGTH: 49
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 1
taatacgact cactataggg agacacagaa ctggatgttg ctgctggag                49

<210> SEQ ID NO 2
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 2
catgaacctg tcaatcttct                20

<210> SEQ ID NO 3
<211> LENGTH: 21
<212> TYPE: DNA
<213> ORGANISM: Homo sapiens

<400> SEQUENCE: 3
ggaaggtgcc catgccagag a                21

```
<210> SEQ ID NO 4
<211> LENGTH: 48
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 4
taatacgact cactataggg agagctgcct tcaaggggga ttctggag          48

<210> SEQ ID NO 5
<211> LENGTH: 24
<212> TYPE: DNA
<213> ORGANISM: Homo sapiens

<400> SEQUENCE: 5
agcttctcat tgttgtcctt atcc                                   24

<210> SEQ ID NO 6
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 6
tgttacacag caggggcct                                         20

<210> SEQ ID NO 7
<211> LENGTH: 48
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 7
taatacgact cactataggg agacggccaa catgctcagg gaacaggt          48

<210> SEQ ID NO 8
<211> LENGTH: 25
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 8
caaacatttt gaagagagac cgtcg                                  25

<210> SEQ ID NO 9
<211> LENGTH: 23
<212> TYPE: DNA
<213> ORGANISM: Homo sapiens

<400> SEQUENCE: 9
tttttcttcg ttgcccctca gcc                                    23

<210> SEQ ID NO 10
<211> LENGTH: 21
<212> TYPE: DNA
```

```
<213> ORGANISM: Homo sapiens

<400> SEQUENCE: 10
tgcccaggat tgattcacag g                                              21

<210> SEQ ID NO 11
<211> LENGTH: 20
<212> TYPE: DNA
<213> ORGANISM: Homo sapiens

<400> SEQUENCE: 11
aggccagaag gaatgatggg                                                20

<210> SEQ ID NO 12
<211> LENGTH: 20
<212> TYPE: DNA
<213> ORGANISM: Homo sapiens

<400> SEQUENCE: 12
ctaagcccaa agtgtggatc                                                20

<210> SEQ ID NO 13
<211> LENGTH: 53
<212> TYPE: DNA
<213> ORGANISM: Homo sapiens

<400> SEQUENCE: 13
gaaattaata cgactcacta tagggagaac cctttctca ggacctctgg agg             53

<210> SEQ ID NO 14
<211> LENGTH: 24
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 14
acagaggtcc tgagaaaagg gtct                                           24

<210> SEQ ID NO 15
<211> LENGTH: 52
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 15
taatacgact cactataggg agactatgaa tcatttgaag aacttactgg ag             52

<210> SEQ ID NO 16
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 16
ctgcagacat ttccttttct                                                20
```

```
<210> SEQ ID NO 17
<211> LENGTH: 23
<212> TYPE: DNA
<213> ORGANISM: Homo sapiens

<400> SEQUENCE: 17
gcatctggcc gaggcttttc tac                                              23

<210> SEQ ID NO 18
<211> LENGTH: 23
<212> TYPE: DNA
<213> ORGANISM: Homo sapiens

<400> SEQUENCE: 18
gttcgacagt cagccgcatc ttc                                              23

<210> SEQ ID NO 19
<211> LENGTH: 23
<212> TYPE: DNA
<213> ORGANISM: Homo sapiens

<400> SEQUENCE: 19
tgatgccccc atgttcgtca tgg                                              23

<210> SEQ ID NO 20
<211> LENGTH: 22
<212> TYPE: DNA
<213> ORGANISM: Homo sapiens

<400> SEQUENCE: 20
cttccaggag cgagatccct cc                                               22

<210> SEQ ID NO 21
<211> LENGTH: 51
<212> TYPE: DNA
<213> ORGANISM: Homo sapiens

<400> SEQUENCE: 21
gtaatacgac tcactatagg gcggggtgct aagcagttgg tggtgctgga g               51

<210> SEQ ID NO 22
<211> LENGTH: 26
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 22
cagcctcaag atcatcagca atgcct                                           26

<210> SEQ ID NO 23
<211> LENGTH: 54
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 23
taatacgact cactataggg agactcaagg gcatcctggg ctacactgga gcac            54

<210> SEQ ID NO 24
```

```
<211> LENGTH: 25
<212> TYPE: DNA
<213> ORGANISM: Homo sapiens

<400> SEQUENCE: 24
gaggtccacc accctgttgc tgtag                                              25

<210> SEQ ID NO 25
<211> LENGTH: 29
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 25
gttgaagtca gaggagacca cctggtgct                                          29

<210> SEQ ID NO 26
<211> LENGTH: 47
<212> TYPE: DNA
<213> ORGANISM: Homo sapiens

<400> SEQUENCE: 26
taatacgact cactataggg agaggaataa ccctgcagaa actggag                      47

<210> SEQ ID NO 27
<211> LENGTH: 24
<212> TYPE: DNA
<213> ORGANISM: Homo sapiens

<400> SEQUENCE: 27
cccttccccc aaaaacaaca atga                                               24

<210> SEQ ID NO 28
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 28
cctggtctgt tttggcatct                                                    20

<210> SEQ ID NO 29
<211> LENGTH: 23
<212> TYPE: DNA
<213> ORGANISM: Homo sapiens

<400> SEQUENCE: 29
attctgccct cgagcccacc ggg                                                23

<210> SEQ ID NO 30
<211> LENGTH: 23
<212> TYPE: DNA
<213> ORGANISM: Homo sapiens

<400> SEQUENCE: 30
caaacaaatt cggtacatcc tcg                                                23

<210> SEQ ID NO 31
<211> LENGTH: 23
```

```
<210> SEQ ID NO 31
<211> LENGTH: 23
<212> TYPE: DNA
<213> ORGANISM: Homo sapiens

<400> SEQUENCE: 31
tggattcaat gaggagactt gcc                                           23

<210> SEQ ID NO 32
<211> LENGTH: 51
<212> TYPE: DNA
<213> ORGANISM: Homo sapiens

<400> SEQUENCE: 32
gtaatacgac tcactatagg gcgcctcact actctcaaat ctgttctgga g            51

<210> SEQ ID NO 33
<211> LENGTH: 27
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 33
ggagtttgag gtatacctag agtacct                                       27

<210> SEQ ID NO 34
<211> LENGTH: 48
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 34
taatacgact cactataggg agacctgagg gctcttcggc aaatgtag                48

<210> SEQ ID NO 35
<211> LENGTH: 25
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 35
aatgggcatt ccttcttctg gtcag                                         25

<210> SEQ ID NO 36
<211> LENGTH: 26
<212> TYPE: DNA
<213> ORGANISM: Homo sapiens

<400> SEQUENCE: 36
gaacaacata agttctgtgc ccagtg                                        26

<210> SEQ ID NO 37
<211> LENGTH: 47
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated
```

```
<400> SEQUENCE: 37
taatacgact cactataggg agacagaaaa catgcccgtc ttcctgg                    47

<210> SEQ ID NO 38
<211> LENGTH: 25
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 38
gcggccagga tataactgac ttcac                                            25

<210> SEQ ID NO 39
<211> LENGTH: 25
<212> TYPE: DNA
<213> ORGANISM: Homo sapiens

<400> SEQUENCE: 39
tccacattca gcacaggact ctctg                                            25

<210> SEQ ID NO 40
<211> LENGTH: 49
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 40
taatacgact cactataggg agaagtgacc tagagctgag tgcctggag                  49

<210> SEQ ID NO 41
<211> LENGTH: 28
<212> TYPE: DNA
<213> ORGANISM: Homo sapiens

<400> SEQUENCE: 41
ctctcagagc aaacaatcac aaacacac                                         28

<210> SEQ ID NO 42
<211> LENGTH: 19
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 42
tcgaagcttc tggacccct                                                   19

<210> SEQ ID NO 43
<211> LENGTH: 52
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 43
taatacgact cactataggg agagaggtga tagtgtggtt tatggactgg ag              52
```

<210> SEQ ID NO 44
<211> LENGTH: 22
<212> TYPE: DNA
<213> ORGANISM: Homo sapiens

<400> SEQUENCE: 44
caacggggat ggccttgtat gc                                                  22

<210> SEQ ID NO 45
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 45
aacttcttag attttgacct                                                     20

<210> SEQ ID NO 46
<211> LENGTH: 22
<212> TYPE: DNA
<213> ORGANISM: Homo sapiens

<400> SEQUENCE: 46
acagaaacac ttttcgacat ag                                                  22

<210> SEQ ID NO 47
<211> LENGTH: 22
<212> TYPE: DNA
<213> ORGANISM: Homo sapiens

<400> SEQUENCE: 47 aaggggagc ctcaccacga gc                                                   22

<210> SEQ ID NO 48
<211> LENGTH: 22
<212> TYPE: DNA
<213> ORGANISM: Homo sapiens

<400> SEQUENCE: 48
cgtgagcgct tcgagatgtt cc                                                  22

<210> SEQ ID NO 49
<211> LENGTH: 51
<212> TYPE: DNA
<213> ORGANISM: Homo sapiens

<400> SEQUENCE: 49
gtaatacgac tcactatagg gcgaccctt ttggacttca ggtggctgga g                   51

<210> SEQ ID NO 50
<211> LENGTH: 25
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 50
gagccagggg ggagcagggc tcact                                               25

<210> SEQ ID NO 51
<211> LENGTH: 23
<212> TYPE: DNA
<213> ORGANISM: Homo sapiens

<400> SEQUENCE: 51
gggataacac actgcaagtg gac                                              23

<210> SEQ ID NO 52
<211> LENGTH: 24
<212> TYPE: DNA
<213> ORGANISM: Homo sapiens

<400> SEQUENCE: 52
ccacgagccc aagggctacc atgc                                             24

<210> SEQ ID NO 53
<211> LENGTH: 25
<212> TYPE: DNA
<213> ORGANISM: Homo sapiens

<400> SEQUENCE: 53
cgctggagcc gctgcccatc gtgta                                            25

<210> SEQ ID NO 54
<211> LENGTH: 51
<212> TYPE: DNA
<213> ORGANISM: Homo sapiens

<400> SEQUENCE: 54
gtaatacgac tcactatagg gcgggcggga cctcagctgc acttgctgga g               51

<210> SEQ ID NO 55
<211> LENGTH: 25
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 55
cagctgtcca acatgatcgt gcgct                                            25

<210> SEQ ID NO 56
<211> LENGTH: 47
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 56
taatacgact cactataggg agactctgcc tcctcctgcc tgtctgc                    47

<210> SEQ ID NO 57
<211> LENGTH: 25
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 57

-continued cggcatcaag gcacagggga ccagt                                         25

<210> SEQ ID NO 58
<211> LENGTH: 25
<212> TYPE: DNA
<213> ORGANISM: Homo sapiens

<400> SEQUENCE: 58
cttcaacagt gcccaaggtg ctcaa                                         25

<210> SEQ ID NO 59
<211> LENGTH: 49
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 59
ttagggaacc ctcactgaat gaatgaatga atgaatgaat gaatgaatg               49

<210> SEQ ID NO 60
<211> LENGTH: 25
<212> TYPE: DNA
<213> ORGANISM: Homo sapiens

<400> SEQUENCE: 60
cattcattca ttcagtgagg gttcc                                         25

<210> SEQ ID NO 61
<211> LENGTH: 48
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 61
taatacgact cactataggg agacatcgac aaggtgcgct tcctggag                48

<210> SEQ ID NO 62
<211> LENGTH: 22
<212> TYPE: DNA
<213> ORGANISM: Homo sapiens

<400> SEQUENCE: 62
cgcgggcttt gtcgttggtt ag                                            22

<210> SEQ ID NO 63
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 63
caggatctta ttctgctgct                                               20

<210> SEQ ID NO 64
<211> LENGTH: 48
<212> TYPE: DNA

```
<213> ORGANISM: Homo sapiens

<400> SEQUENCE: 64
taatacgact cactataggg agaccccttt ttgtccccca actggaga                48

<210> SEQ ID NO 65
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 65
ccaaaagcct tcatacatct                                               20

<210> SEQ ID NO 66
<211> LENGTH: 32
<212> TYPE: DNA
<213> ORGANISM: Homo sapiens

<400> SEQUENCE: 66
aaggtgtgca cttttattca actggtctca ag                                 32

<210> SEQ ID NO 67
<211> LENGTH: 49
<212> TYPE: DNA
<213> ORGANISM: Homo sapiens

<400> SEQUENCE: 67
taatacgact cactataggc tggctggttt attgctgata aatctggag               49

<210> SEQ ID NO 68
<211> LENGTH: 60
<212> TYPE: DNA
<213> ORGANISM: Homo sapiens

<400> SEQUENCE: 68
tttttttttt tttttttttt tttttttttt ccaatgctta atcagtgagg cacctatctc   60

<210> SEQ ID NO 69
<211> LENGTH: 21
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 69
cgagacccac gctcaccggc t                                             21

<210> SEQ ID NO 70
<211> LENGTH: 48
<212> TYPE: DNA
<213> ORGANISM: Homo sapiens

<400> SEQUENCE: 70
taatacgact cactataggg cacccagaaa cgctggtgaa agtaaaag                48

<210> SEQ ID NO 71
<211> LENGTH: 51
<212> TYPE: DNA
<213> ORGANISM: Homo sapiens
```

-continued

```
<220> FEATURE:
<221> NAME/KEY: modified_base
<222> LOCATION: (1)..(1)
<223> OTHER INFORMATION: Biotinylated

<400> SEQUENCE: 71
taatacgact cactataggg agaggaaaac tgggtgcaga gggttctgga g         51

<210> SEQ ID NO 72
<211> LENGTH: 24
<212> TYPE: DNA
<213> ORGANISM: Homo sapiens

<400> SEQUENCE: 72
ggcaacccta caacagaccc acac                                       24

<210> SEQ ID NO 73
<211> LENGTH: 20
<212> TYPE: DNA
<213> ORGANISM: Homo sapiens
<220> FEATURE:
<221> NAME/KEY: modified_base
<222> LOCATION: (1)..(1)
<223> OTHER INFORMATION: Biotinylated

<400> SEQUENCE: 73
agccctcttc aaaaacttct                                            20
```